United States Patent [19]
Mills

[11] Patent Number: 5,978,691
[45] Date of Patent: Nov. 2, 1999

[54] DEVICE AND METHOD FOR NONINVASIVE CONTINUOUS DETERMINATION OF BLOOD GASES, PH, HEMOGLOBIN LEVEL, AND OXYGEN CONTENT

[76] Inventor: Alexander Knight Mills, Rte. 2, Box 114, Bland, Mo. 65014

[21] Appl. No.: 08/891,354

[22] Filed: Jul. 10, 1997

Related U.S. Application Data

[60] Provisional application No. 60/023,600, Jul. 19, 1996.
[51] Int. Cl.[6] ........................................................ A61B 5/00
[52] U.S. Cl. .............................. 600/334; 600/326; 356/41
[58] Field of Search ...................................... 600/322, 323, 600/326, 334, 344; 356/39, 41

[56] References Cited

U.S. PATENT DOCUMENTS

| | | | |
|---|---|---|---|
| 4,097,921 | 6/1978 | Raffaele | 364/416 |
| 4,167,331 | 9/1979 | Nielsen | 356/39 |

(List continued on next page.)

FOREIGN PATENT DOCUMENTS

| | | | |
|---|---|---|---|
| WO 90/00572 | 1/1990 | WIPO | C08G 18/32 |

OTHER PUBLICATIONS

Steven J. Baker; Monitoring Oxygen and Carbon Dioxide; Oct. 21, 1986.
Jonas A. Pologe; Pulse Oximetry: Technical Aspects of Machine Design; pp. 137–153; date unknown.
Helen M. Ranner and Vijay Sharma; Structure and function of hemogolbin; Williams Hemotology, Fifth Edition; Mcgraw Hill, Inc.; pp. 417–425.
A H J Maas, P. Rispens, O. Siggard–Andersen, and W. G. Zijlstra; In the reliability of the Henderson–Hasselbalch equation in routine clinical acid–base chemistry; Annanls of Clinical Biochemistry; vol. 21; 1984.
A. Gerson Greenburg and Peter V. Moulder; Temperature Coefficients for PCO2 and pH in Whole Blood; Arch. Surg., vol. 91, Dec. 1965; pp. 867–871.

Ole Siggaard–Andersen, Peter D. Wimberly, Ivar Gothgen, and Mads Siggaard–Andersen; A Mathematical Model of the Hemoglobin–Oxygen Dissociation Cuve of Human Blood and ot the Oxygen Partial Pressure as a Function of Temperature; Clinical Chemistry, vol. 30, No. 10, 1984; pp. 1646–1651.
G.R. Kelman and J.F. Nunn; Nomogrtams for correction of blood PO2, PCO2, pH, and Base excess for time and temperature; Journal of Applied Physiology, vol. 21, 1966; pp. 1484–1490.
P. Astrup, K. Engel, J.W. Severinghaus and E. Munson; The Influence of Temperature and pH on the Dissociation Curve of Oxyhemoglobin of Human Blood; The Scandinavian Journal of Clinical & Laboratory Investigation; vol.17, No.6, 1965; pp. 515–523.
Horace W. Davenport; The ABC of Acid–Base Chemistry; The Univ. of Chicago Press, Fifth Edition, Revised; pp. 8–49, and 50–68.
J.F. Nunn; Nunn's Applied Respiratory Physiology; Fourth Edition; Butterworth Heinemann; Chapters 10 and 11, pp. 219–246, and 247–305.
J. W. Severinghaus, M. Stuppel, and A. F. Bradley; Variations of Serum Carbonic Acid pK with pm and Temperature; Journal of Applied Physiology, vol. 9, 1956; pp. 197–199.

*Primary Examiner*—Max Hindenburg
*Assistant Examiner*—Eric F. Winakur

[57] ABSTRACT

A device and method for noninvasively quantifying important physiological parameters in blood. The device and method utilizes changes in molecular behavior induced by thermal energy of change to facilitate the measurement of the physiological parameters in blood. Oxygen saturation, partial pressure of oxygen, partial pressure of carbon dioxide, concentration of bicarbonate ion and total carbon dioxide, acid-base balance, base excess, hemoglobin level, hematocrit, oxyhemoglobin level, deoxyhemoglobin level, and oxygen content can all be determined quickly, easily, and continuously. There is no need for skin puncture or laboratory analysis.

48 Claims, 13 Drawing Sheets

U.S. PATENT DOCUMENTS

| | | | |
|---|---|---|---|
| 4,485,820 | 12/1984 | Flower | 128/633 |
| 4,495,211 | 1/1985 | Mooiweer | 426/422 |
| 4,579,641 | 4/1986 | Shemomura et al. | 204/403 |
| 4,615,340 | 10/1986 | Cronenberg et al. | 128/635 |
| 4,704,029 | 11/1987 | Van Heuvelen | 356/39 |
| 4,785,814 | 11/1988 | Kane | 128/634 |
| 4,802,486 | 2/1989 | Goodman et al. | 128/633 |
| 4,805,623 | 2/1989 | Jobsis | 128/633 |
| 4,848,901 | 7/1989 | Hood, Jr. | 356/41 |
| 4,859,257 | 8/1989 | Taylor et al. | 356/41 |
| 4,869,254 | 9/1989 | Stone et al. | 128/633 |
| 4,911,167 | 3/1990 | Corenman et al. | 128/633 |
| 4,911,230 | 3/1990 | Mayer et al. | 165/48.1 |
| 4,926,867 | 5/1990 | Kanda et al. | 600/334 |
| 4,928,691 | 5/1990 | Nicolson et al. | 128/633 |
| 4,928,692 | 5/1990 | Goodman et al. | 128/633 |
| 4,934,372 | 6/1990 | Corenman et al. | 128/633 |
| 5,006,105 | 4/1991 | Sherard | 600/22 |
| 5,009,505 | 4/1991 | Malvern | 356/352 |
| 5,055,671 | 10/1991 | Jones | 250/227.21 |
| 5,078,136 | 1/1992 | Stone et al. | 128/633 |
| 5,101,825 | 4/1992 | Gravenstein et al. | 128/633 |
| 5,131,391 | 7/1992 | Sakai et al. | 600/334 |
| 5,190,039 | 3/1993 | Takeuchi et al. | 600/323 |
| 5,284,139 | 2/1994 | Khalil et al. | 128/634 |
| 5,293,875 | 3/1994 | Stone | 128/719 |
| 5,337,744 | 8/1994 | Branigan | 128/633 |
| 5,351,686 | 10/1994 | Steuer et al. | 128/633 |
| 5,355,882 | 10/1994 | Ukawa et al. | 128/633 |
| 5,357,971 | 10/1994 | Sheehan et al. | 128/719 |
| 5,362,966 | 11/1994 | Rosenthal et al. | 250/341.1 |
| 5,372,136 | 12/1994 | Steuer et al. | 128/633 |
| 5,402,777 | 4/1995 | Warring et al. | 604/307 |
| 5,404,885 | 4/1995 | Sheehan et al. | 128/716 |
| 5,412,510 | 5/1995 | Iizuka et al. | 359/820 |
| 5,414,648 | 5/1995 | Morgan et al. | 364/563 |
| 5,421,329 | 6/1995 | Casciani et al. | 128/633 |
| 5,423,327 | 6/1995 | Clauson et al. | 128/716 |
| 5,427,093 | 6/1995 | Ogawa et al. | 128/633 |
| 5,428,323 | 6/1995 | Geissler et al. | 333/135 |
| 5,431,159 | 7/1995 | Baker et al. | 128/633 |
| 5,433,197 | 7/1995 | Stark | 128/633 |
| 5,445,157 | 8/1995 | Adachi et al. | 128/664 |
| 5,448,992 | 9/1995 | Kupershmidt | 128/633 |
| 5,452,717 | 9/1995 | Branigan et al. | 128/633 |
| 5,453,248 | 9/1995 | Olstein | 422/82.07 |
| 5,462,052 | 10/1995 | Gehrich et al. | 128/632 |
| 5,469,845 | 11/1995 | DeLonzor et al. | 128/633 |
| 5,480,723 | 1/1996 | Klainer et al. | 428/441 |
| 5,492,118 | 2/1996 | Gratton et al. | 128/633 |
| 5,497,771 | 3/1996 | Rosenheimer | 128/633 |
| 5,503,148 | 4/1996 | Pologe et al. | 128/633 |
| 5,517,987 | 5/1996 | Tsuchiya | 600/328 |
| 5,526,808 | 6/1996 | Kaminsky | 128/632 |
| 5,536,783 | 7/1996 | Olstein et al. | 525/129 |
| 5,553,615 | 9/1996 | Carim et al. | 128/633 |
| 5,604,584 | 2/1997 | Iwasaki | 356/218 |
| 5,607,644 | 3/1997 | Olstein et al. | 422/82.07 |
| 5,632,958 | 5/1997 | Kane et al. | 422/82.07 |
| 5,642,734 | 7/1997 | Ruben et al. | 128/693 |
| 5,656,241 | 8/1997 | Seifert et al. | 422/82.06 |
| 5,672,515 | 9/1997 | Furlong | 436/133 |
| 5,681,532 | 10/1997 | Kane et al. | 422/82.06 |

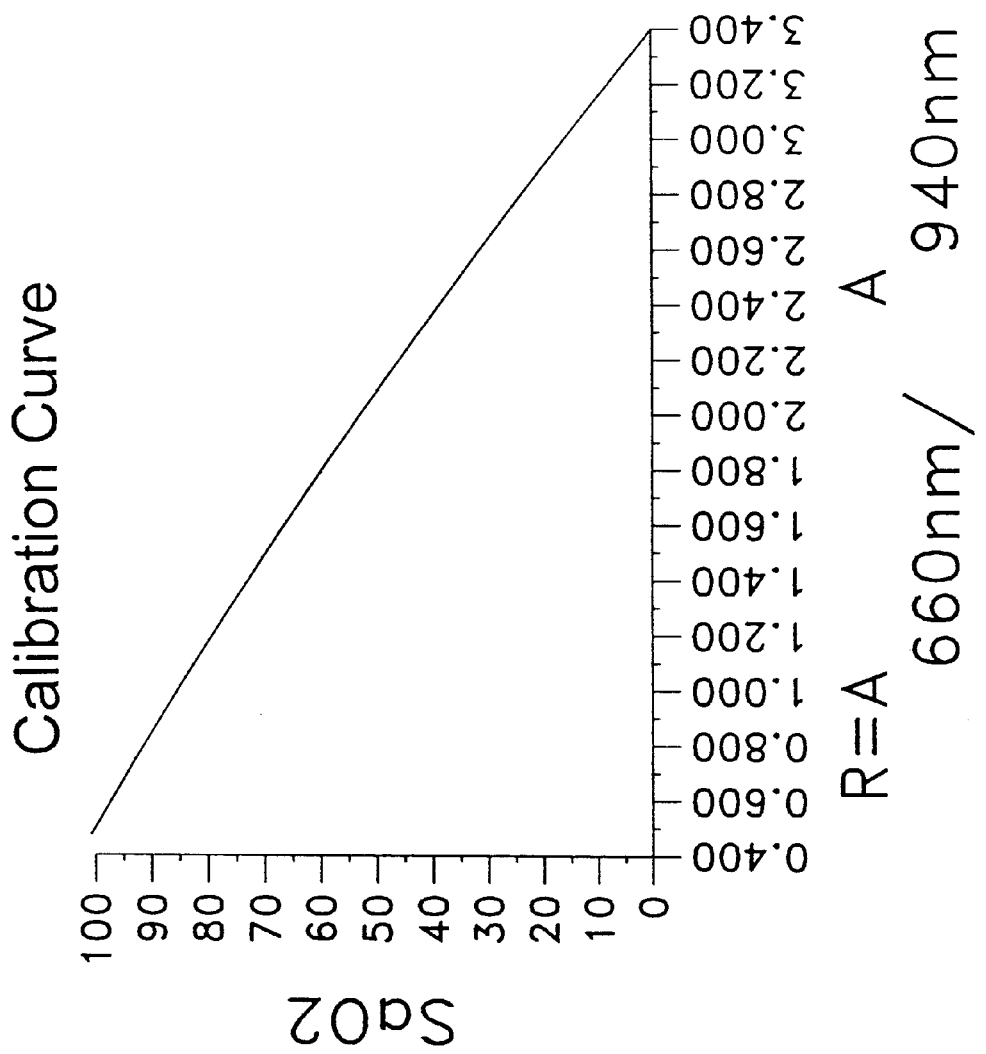

DEVICE AND METHOD FOR NONINVASIVE CONTINUOUS DETERMINATION OF BLOOD GASES, PH, HEMOGLOBIN LEVEL, AND OXYGEN CONTENT

This application claims benefit of provisional application Ser. No. 60/023,600 filed Jul. 19, 1996.

BACKGROUND OF THE INVENTION

1. Field of the Invention

This invention generally relates to a noninvasive method of quantitatively determining the concentration of components in a light- or other radiation-scattering environment. A novel means of varying temperature or other parameters to assist in determinations is presented.

More particularly, the invention relates to spectrophotometry systems and measurements of behavior, action or function of substances which are affected by temperature or other variables.

A method and device for the continuous monitoring of blood parameters is especially disclosed. This technology makes use of measurement of temperature-induced changes in the respiratory molecule hemoglobin to determine acid-base balance and other parameters.

2. Description of the Related Art

There is no device currently known which can noninvasively measure pH and/or blood gases.

In a broad context, differential thermal analysis is a technique used in analytical chemistry for identifying and quantitatively analyzing the chemical composition of substances by observing the thermal behavior of a sample as it is heated. This methodology is widely used for identifying minerals and mineral structures, but is not performed noninvasively and is in fact usually destructive to the sample being tested. It is not useful in biologic applications. Similarly, related thermometric methods such as thermogravimetry, calorimetry, and cryoscopy are not related to the present invention.

Induction of temperature changes has been used in the experimental study of chemical kinetics to facilitate measurement of reaction rates. The technique described herein does not depend upon any chemical reaction taking place.

Temperature is a very important factor in the chemistry of both biologic and non-biologic systems. It reckons in the speed of reactions; indeed, if a reaction will occur at all. Temperature can be relatively easy to both measure and regulate. Furthermore, changing the temperature of a substance or system does not normally damage the substance in any way (within a certain range; clearly temperature extremes will harm almost any system). Temperature by itself can affect acid-base balance and pH because of a direct affect on the hydrogen ion.

Spectrophotometry is a commonly used technique for the identification and quantification of substances. It is used in medicine in the form of pulse oximetry, to determine the ratio of oxyhemoglobin to deoxyhemoglobin and thus measure the oxygenation status of a patient. Spectrophotometry deals with measurement of the radiant energy transmitted or reflected by a body as a function of the wavelength. Infrared (IR) spectroscopy passes infrared light through an organic molecule and produces a spectrum that can be plotted as the amount of light transmitted versus the wavelength of infrared radiation. Since all bonds in an organic molecule interact with infrared radiation, IR spectra provide a great deal of structural data, allowing identification to be made. There is a large area of prior art relating to spectrophotometry and, more specifically, to oximetry. The most relevant prior art known by the inventor is reviewed below, but none relate to the unique determinations made possible by the method and device disclosed in this application.

U.S. Pat. No. 5,431,159, issued Jul. 11, 1995 to Baker et al, describes methods of improving measurements made by standard pulse oximetry. While these devices may improve the signal quality and signal-to-noise ratio for oximeter calculations, they do not allow for any new determinations, as outlined in the present application.

U.S. Pat. No. 5,101,825, issued Apr. 7, 1982 to Gravenstein et al, purports to measure hemoglobin noninvasively by means of simultaneous measurement of volume changes and changes in the mass of hemoglobin species measured by oximetry. It is unclear how blood volume changes could be determined to the desired accuracy.

U.S. Pat. No. 5,499,627, issued Mar. 19, 1996 to Steuer et al, claims a system for noninvasive hematocrit monitoring. The patent describes techniques of measuring the infrared absorption of hemoglobin at isobestic points of the oxy and deoxy species. However, there is no discussion relating to the use of temperature changes and, therefore, Steuer et al. is not particularly relavent to the present invention.

U.S. Pat. No. 5,427,093, issued Jun. 27, 1995 to Ogawa et al, describes a device to disperse heat generated by the LED in an oximeter probe by means of a heat-dissipating plate. This is a potential benefit for standard pulse oximeters, but in no way improves their measurements or allow for new determinations, as in the device and method described herein.

U.S. Pat. No. 4,167,331, issued Sep. 11, 1979 to Nielsen, teaches the use of multiple wavelength techniques for identification of multiple absorbing substances.

Several patents claim the non-invasive measurement of blood glucose using modified light radiation. U.S. Pat. No. 4,704,029, issued Nov. 3, 1987 to Van Heuvelen, discloses the measurement of blood glucose by utilizing a refractometer. U.S. Pat. No. 5,448,992, issued Sep. 12, 1995 to Kupershmidt, bases measurements on a polarized-modulated laser. U.S. Pat. No. 5,433,197 to Stark describes non-invasive glucose measurement using irradiation of the eye. There are many other such references, but none relate specifically to the technique of this application.

U.S. Pat. No. 4,805,623, issued Feb. 21, 1989 to Jobsis, describes a spectrophotometric method of determining the concentration of a dilute component together with a reference component of known concentration. While not similar to the technology here disclosed, the patent teaches that obtaining an appropriate reference component is often problematic. The technique outlined in the present application obviates this lack of reference components for many cases, as determination of the concentration of many substances, such as hemoglobin level, in blood or other environments can now be done, and they in turn can serve as reference components.

U.S. Pat. No. 5,492,118, issued Feb. 20, 1996 to Gratton et al, also discloses a technique for determining material (specifically glucose) concentrations in tissues. This is done by measuring the scattering coefficient of light passed through the tissue and comparing this with a previous scattering coefficient determined with respect to the tissue.

U.S. Pat. No. 5,402,777, issued Apr. 4, 1995 to Warring et al, describes a device to facilitate non-invasive oxygen monitoring. This is a sensor system designed to improve the performance of a pulse oximeter under certain circumstances. While this may be a useful aid in standard pulse oximetry, it in no way enables any additional determinations to be made, as in the device described in the present invention.

Additionally, many patents disclose improvements to pulse oximeter probes or sensor as advances in the art. Included in this group is U.S. Pat. No. 5,469,845 DeLonzor et al, and many others.

3. Physiology and Biochemistry Background

This section refers specifically to hemoglobin and oximetry. Changes in many other substances secondary to thermal effects also occur, and measurements and determinations based on these effects are meant to be included within the scope of this patent application.

Hemoglobin is the molecule which is essentially entirely responsible for carrying oxygen in all vertebrates and some invertebrates (See; *Nunn's Applied Respiratory Physiology*, Cambridge, Mass.; Butterworth-Heinemann, 4th Edition (1993), Chapter 10, pp 219–246); the remainder of this discussion will be limited to humans. It is contained in the red blood cell (RBC, erythrocyte), which is the most common cell in the body. A molecule or single unit of hemoglobin (Hb) contains 4 iron groups, each of which can bind 1 molecule or unit of oxygen. Because there are 4 iron groups, a molecule of Hb can contain from 0 to 4 molecules of $O_2$. Hb which is carrying $O_2$ is known as oxyhemoglobin ($HbO_2$), Hb not carrying oxygen in known as deoxyhemoglobin. The relative number of $O_2$ molecules bound to a Hb molecule is referred to as saturation, expressed in percentage. Of course, blood is composed of billions and billions of RBCs and Hb molecules, so the averaged saturation can take on any value from 0 to 100%.

How well Hb is saturated with $O_2$ depends mainly on the "partial pressure" of oxygen in the blood. The higher the pressure of oxygen in the blood ($PO_2$), the higher the saturation ($SO_2$). However, the relationship between $PO_2$ and $SO_2$ is not linear (change in one is not always directly proportional to change in the other). The dependence is described by a S-shaped "sigmoid" curve, common in the biologic sciences. This particular curve is call the Hemoglobin-Oxygen Dissociation Curve (HODC; see FIG. 1). Hb absorbs $O_2$ in the lungs (to form $HbO_2$). As the RBC travels to the tissues, the $HbO_2$ releases oxygen.

Determination of the physiological parameters is a very important part of modern medical practice. Unfortunately, measurement of any of these parameters has until recently always required a blood sample (arterial and/or venous) to be drawn, which is then analyzed by a laboratory.

During the 1970's the first pulse oximeter was introduced. This device made use of spectrophotometry to allow approximation of arterial oxygen saturation ($SaO_2$), termed $SpO_2$ (saturation measured by pulse oximetry), by noninvasive means. After improvements, pulse oximeters are now commonplace in acute health care settings.

Pulse oximeter design and function are well documented. The two principal forms of Hb (oxy and deoxy: Hb and $HbO_2$) absorb different wavelengths of light to varying degrees. The standard oximeter utilizes 2 wavelengths, one in the "red" portion of the light spectrum and the other in the near-infrared. The absorbance of emissions from light-emitting diodes (LEDs) of appropriate wavelength is measured. The pulsatile (AC) and non-pulsatile (DC) components are calculated and compared, and the ratio of the corrected signal is collated to a stored calibration curve to yield $SpO_2$.

Transcutaneous monitoring of oxygen and carbon dioxide is also used as discussed in S. J. Barker, "Monitoring Oxygen and Carbon Dioxide", *International Anesthesia Research Society*, March 1996, pp 1–7, but there are several practical difficulties with this technology. It is dependent upon cardiac output and skin perfusion, the electrode must be calibrated before application to the skin, and the sensor's membrane and electrolyte must be replaced periodically. The only significant application has been found in neonatology.

There are many references disclosing noninvasive determination of glucose. However, no device has yet found acceptance in the marketplace for this function.

There have also been numerous attempts at monitoring using miniaturized probes passed through arterial cannulae. The first approach employed Clark electrodes, the same oxygen electrode used In the laboratory blood-gas analyzer. More recently, the principle of florescence quenching has been used to develop fiberoptic "optodes" which can continuously monitor pH and $PCO_2$ as well as $PO_2$ through an arterial cannula. Unfortunately, there have been some technical problems with optode accuracy and reliability. While this technology will no doubt improve, it remains very costly and is of course invasive in nature.

Thus, the $SO_2$ can now be determined noninvasively. However, still the only way to determine pH and other parameters accurately has been by drawing a blood sample and utilizing laboratory analysis. Such analysis is obviously invasive (requires breaking the skin; any time the skin barrier is ruptured inflammation and/or infection can ensue), very painful (puncture of an artery is technically more difficult and much more painful than puncture of a vein, which is how most blood tests are performed), risks blood contamination for both the subject and the person drawing the blood, and creates toxic medical waste (syringe, needle, gloves, skin dressing, test tube or other container). It is expensive to perform, not only from the supplies and the cost of the analyzer making the measurement, but the operation of the analyzer and the drawing of the blood both require trained personnel. The analyzer must be calibrated frequently with chemical reagents which are costly and must be disposed of safely. Arterial puncture is also inherently dangerous, as it can cause a clot in the artery, and prevent blood flow "downstream", thus depriving those tissues of oxygen.

Therefore, it would be an advance in the art to provide a system and method to noninvasively and quantitatively assess acid-base balance and related variables. It would be another advance in the art to noninvasively and quantitatively measure hemoglobin level ("blood count") and oxygen content and capacity. It would be yet another improvement in the art to determine all these parameters rapidly and continuously. It would be of great betterment to make these measurements without the need for laboratory analysis, equipment, and personnel. It would be an progression to have a device with such capabilities that is easily transportable that could be used in an ambulance or when conveying a patient from one location to another.

It would be a further advance to have a device for immediate diagnosis of poisoning such as that due to carbon monoxide. It would be advantageous to allow rapid noninvasive screening of blood disorders such as sickle cell anemia.

BRIEF SUMMARY OF THE INVENTION

The subject invention concerns a novel method for noninvasive determination of properties of subject matter and the environment or milieu in which the subject matter exists.

The method utilizes changes in molecules induced by thermal energy to facilitate measurements. In a preferred embodiment, a new and unique method and device for noninvasive determination of oxygen saturation ($SO_2$), partial pressure of oxygen ($PO_2$), partial pressure of carbon dioxide ($PCO_2$), bicarbonate ion ($HCO_3^-$), total carbon dioxide ($TCO_2$), acid-base balance (pH), base excess, total hemoglobin level (Thb), hematocrit (Hct) oxyhemoglobin level, deoxyhemoglobin level, and oxygen content is described.

The HODC is "shifted" to the left or right (as shown in FIGS. 2 and 3 and as discussed in the literature) by three factors: temperature, acid-base balance of the blood, and the concentration of substances called organic phosphates in the blood. The organic phosphates (the principal one is called 2,3-diphosphoglycerate: 2,3-DPG or 2,3-biphosphoglycerate: 2,3-BPG) are molecules which bind to Hb to facilitate oxygen transport. While they are important, disorders are very rare, and virtually all people can be assumed to have normal levels except in exceptional circumstances. They will not be addressed further here.

This leaves temperature and acid-base balance. The effects of these factors have been well described in the references cited. However, the only use of this information has been to "correct" values of blood samples to what they would read at standard temperature and pH.

The technology described herein utilizes the known shifts in the HODC, along with other science, to perform the measurements and calculations necessary to determine all parameters mentioned above. As mentioned, the factors which cause these shifts are well documented, as are the relative degrees of shift due to each factor. By controlling and varying temperature, one can calculate the degree of shift due to thermal effects. Any remaining degree of shift is due to alteration in acid-base balance. As the influence of acid-base balance upon the HODC is known, alterations and status of acid-base balance can be determined.

The oximeter estimates the $SO_2$ of blood. Thus, it is in effect delineating a point on the HODC. Clearly, this is oblivious of any shift in the curve. By measuring $SO_2$ at two or more points at known temperatures, or one point where the temperature is changed to two or more different known values, one can calculate the "standard" curve. Any deviation in measured values from this curve imply an alteration in acid-base status.

In addition, the pH and $PCO_2$ are known to be affected by the temperature of blood, and these effects are quantified in the literature. (See, O. Siggaard-Anderson, *The Acid-Base Status of the Blood,* 4th Edition, pp. 29–91; Baltimore, Md.; Williams & Wilkins (1974), and J. F. Nunn, *Nunn's Appied Respiratory Physiology,* 4th Edition, pp. 247–305; Cambridge, Mass., Bufterworth-Heinemann (1993).

Thus, comparison of saturation values at different known temperatures allows computation of acid-base balance and the parameters which affect it.

As the hemoglobin molecule is the primary buffer for acid-base balance in the body, estimation of hemoglobin level can be made from the degree of buffering effect (see FIG. 4 and H. W. Davenport, *The ABC of Acid-Base Chemistry,* 5th Edition revised, pp. 8–68, Chicago, Ill., University of Chicago Press (1971).

The technique of repetitious determinations made while altering temperature or other variables allows a multitude of additional analyses to be made. The determinations can be made intermittently or continuously.

The invention, together with additional features and advantages thereof, may best be understood by reference to the following description taken in connection with the accompanying illustrative drawings.

BRIEF SUMMARY OF THE FIGURES

FIG. 11 shows a standard calibration curve used in pulse oximeters. The calibration curve is used by the oximeter to calculate arterial oxygen saturation ($SaO_2$) from the ratio (R) of the light absorbed (A) by the tissue being monitored.

DETAILED DESCRIPTION OF THE INVENTION

Figure 1:
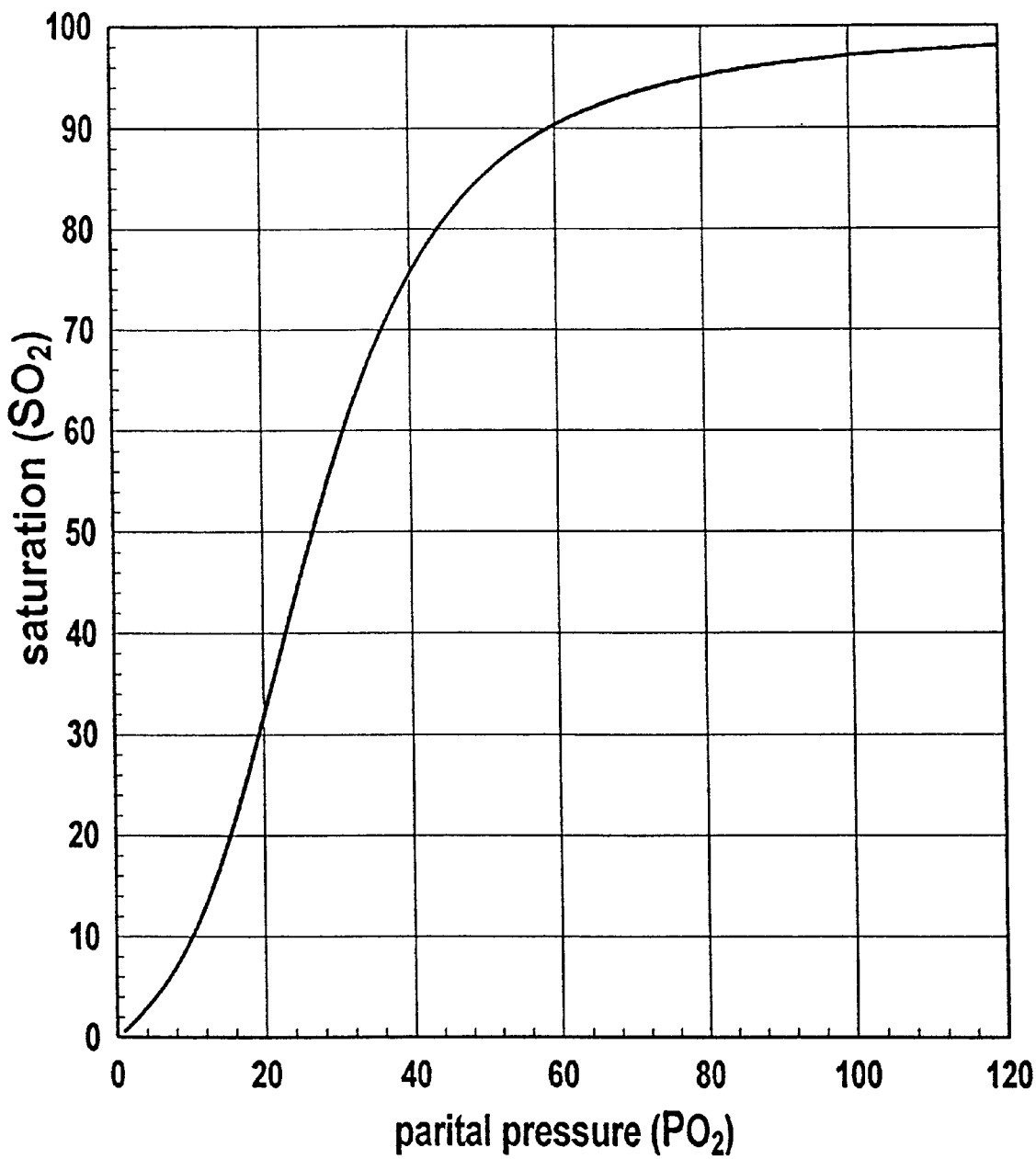
FIG. 1 is a representative graph of the normal hemoglobin-oxygen dissociation curve.
Figure 2:
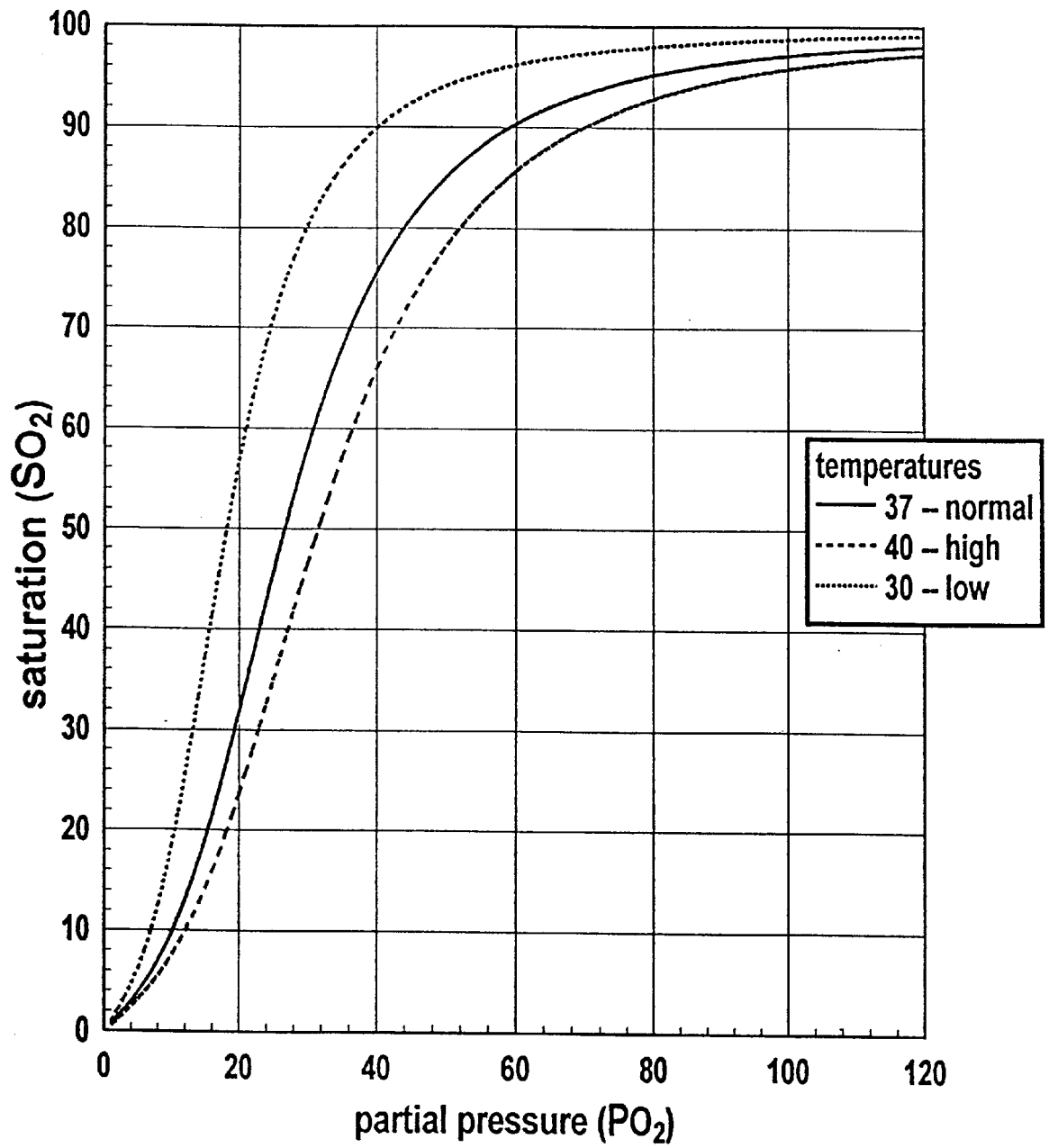
FIG. 2 is a similar graph showing examples of "shifts" or alterations in the hemoglobin-oxygen dissociation curve due to changes in temperature.
Figure 3:
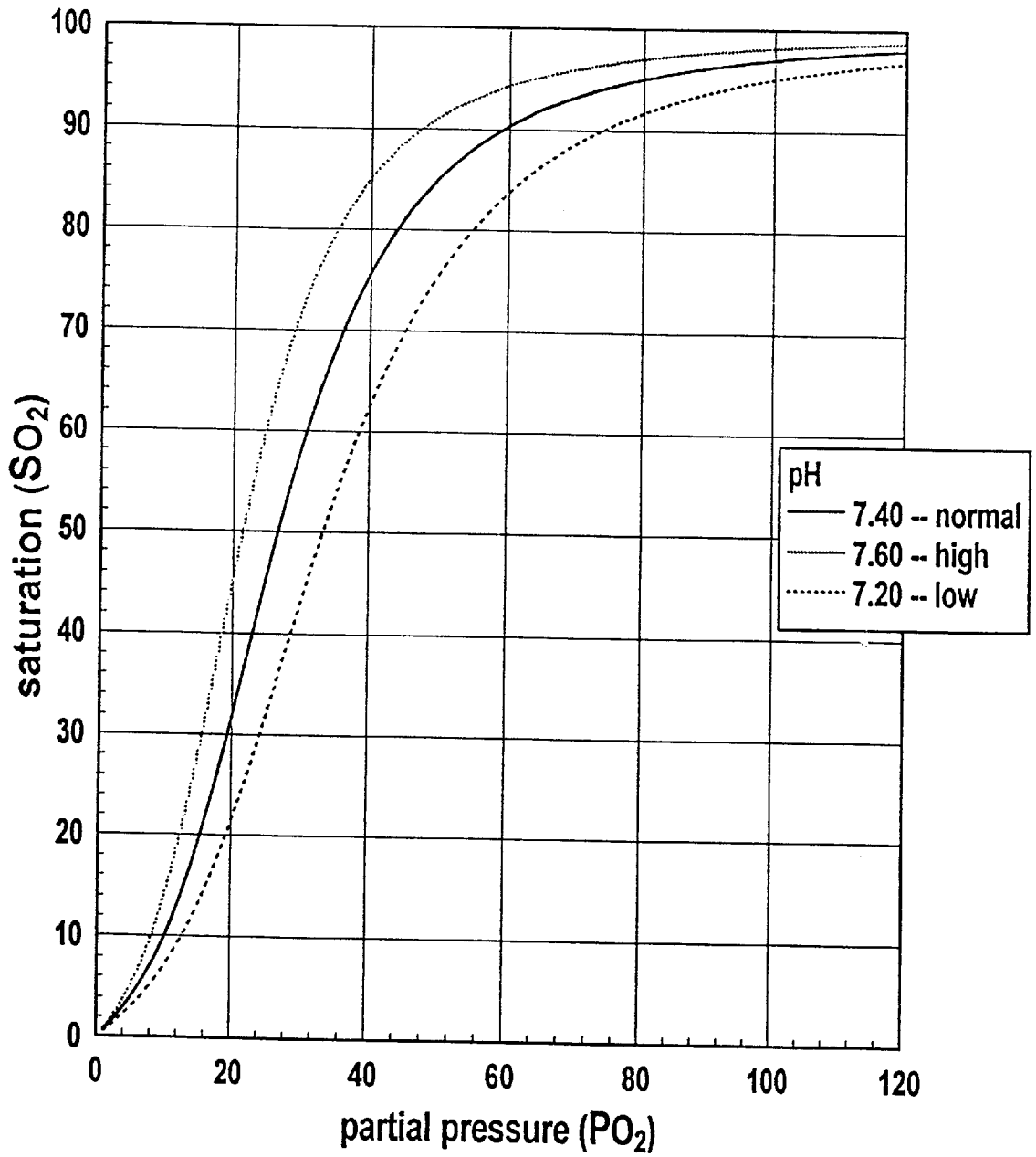
FIG. 3 is a similar graph showing examples of "shifts" or alterations in the hemoglobin-oxygen dissociation curve due to changes in acid-base (pH) status of the blood.

Many forms of electromagnetic radiation can be used to aid in identification of, or to provide other relevant information about molecules, or substances, or their environment. The invention herein utilizes induced temperature changes to assist and improve these measurements, and enables determinations not previously possible. The description which follows is in reference to the study of blood, but can be applied to other substances as well.

All matter is affected by electromagnetic radiation and heating. The longer radio waves induce chiefly thermal agitation of molecules and excitation of molecular rotations, while infrared rays excite vibrational modes of large molecules and release fluorescent emission as well as heat. These effects are documented in standard texts and reference works of physical chemistry. However, many biologic molecules, and a great number of other substances, exhibit effects or behavior when exposed to temperature variation which are not directly attributable to thermal energy. These indirect effects can be used to aid in identification of, or to provide other relevant information about, the molecule or substance or its environment. The invention herein detailed enables measurements and determinations of these effects. The description which follows is in reference to study of the hemoglobin molecule, but extension to other substances ensues clearly.

One part of the invention consists of methods of spectrophotometry and oximetry commonly employed in the practice of medicine. Another part of the invention consists of a device used to induce temperature changes in blood or other media. Included herein are algorithms for the calculation of variables not measured directly. The algorithm outlined below serves as an example, but modifications are possible to arrive at the indicated results, and are meant to be included within the spirit or this invention. In a preferred embodiment, the invention consists of a radiation delivery device 10 for facilitating the noninvasive monitoring of a characteristic of a patient's blood parameters. The device 10 as shown in FIGS. 5a–c and 6 is used to induce temperature changes in the blood. The device 10 includes a radiation emitter 12 having at least one wavelength being applied through a patient's tissue (T) to the patient's blood; a radiation detector 14 which detects reception of the at least one wavelength after absorbance through the blood; a temperature induction generator 16 for inducing temperature changes in the blood; and a controller 18 for computing the various blood parameters based on the absorbance of the at least one wavelength of radiation at various temperature levels of the blood. The radiation emitter 12, detector 14, temperature induction generator 16 are all inserted in a probe 20 which can be placed about the tissue/blood to be measured.

The probe 20 may also include a temperature sensing or measuring device 22 so that the temperature of the tissue and blood can be accurately determined. The controller 18 includes a computing device or standard personal computer (PC) with a monitor 24. Included within the controller are algorithms for the calculation of variables not measured directly. The algorithm outlined below serves as an example, but modifications are possible to arrive at the indicated results, and are meant to be included within the spirit of this application. Various additional components of the device 10 will be discussed in more detail below with reference to Examples 1–18.

The normal temperature of the human body is defined to be 37° centigrade, the normal pH is defined to be 7.40, and the normal base excess is defined to be 0. These values are not necessary for the practice of the invention, but serve as reference points for values in the current medical literature.

Of note, the hemoglobin level and oxygenation of the blood in the arterial circulation is the same no matter where measured, as blood is thoroughly mixed in the left heart before ejection. Thus, the probes could be on fingers, toes, lips, etc., or any combination of these.

Figure 6:
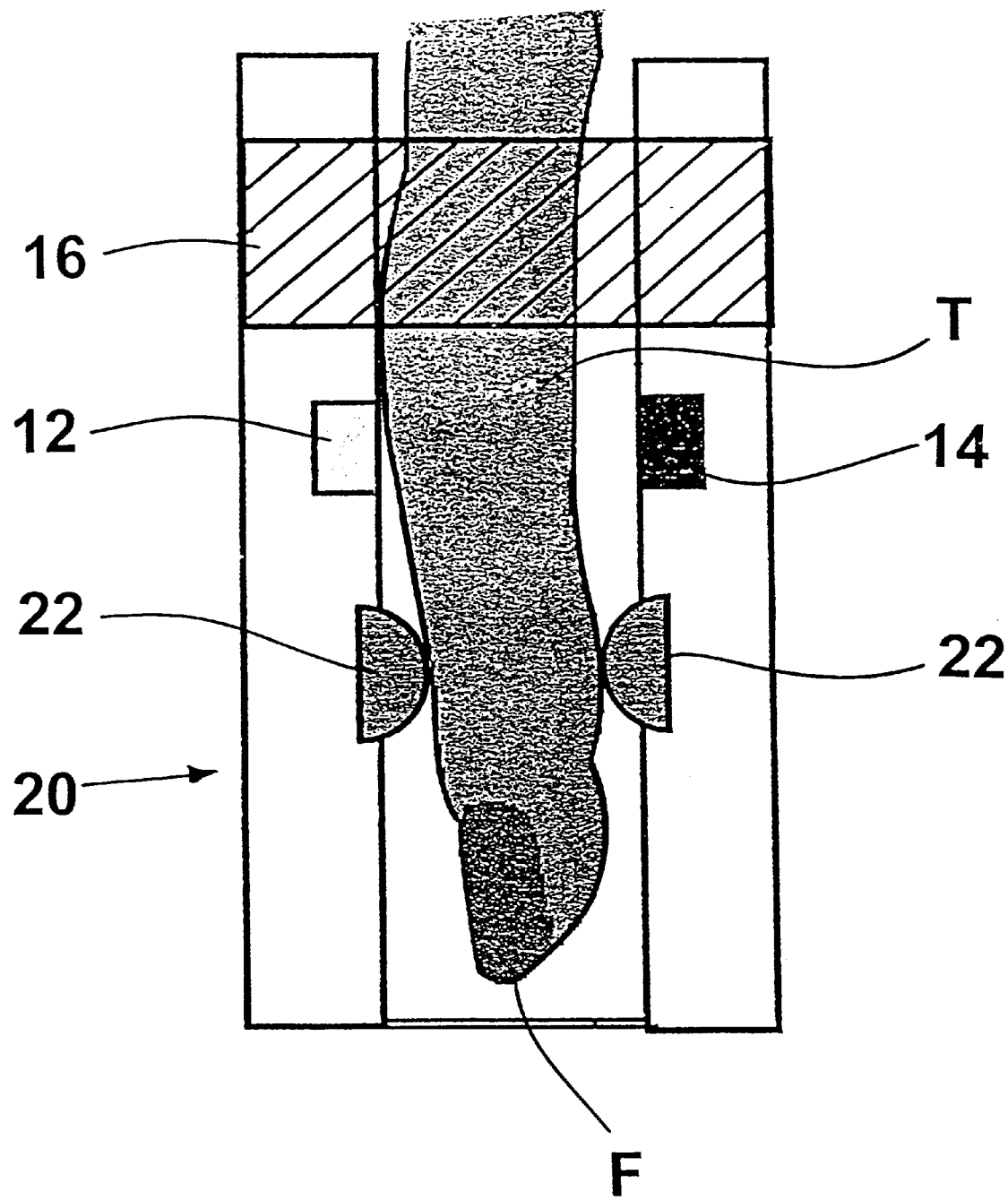
FIG. 6 is a close-up of an embodiment of a probe for use on a finger. The temperature induction and measurement instrumentation are included, as are radiation emission and detection means. Information would be relayed between the probe and additional components (processing, entry, and display units).
Figure 9:
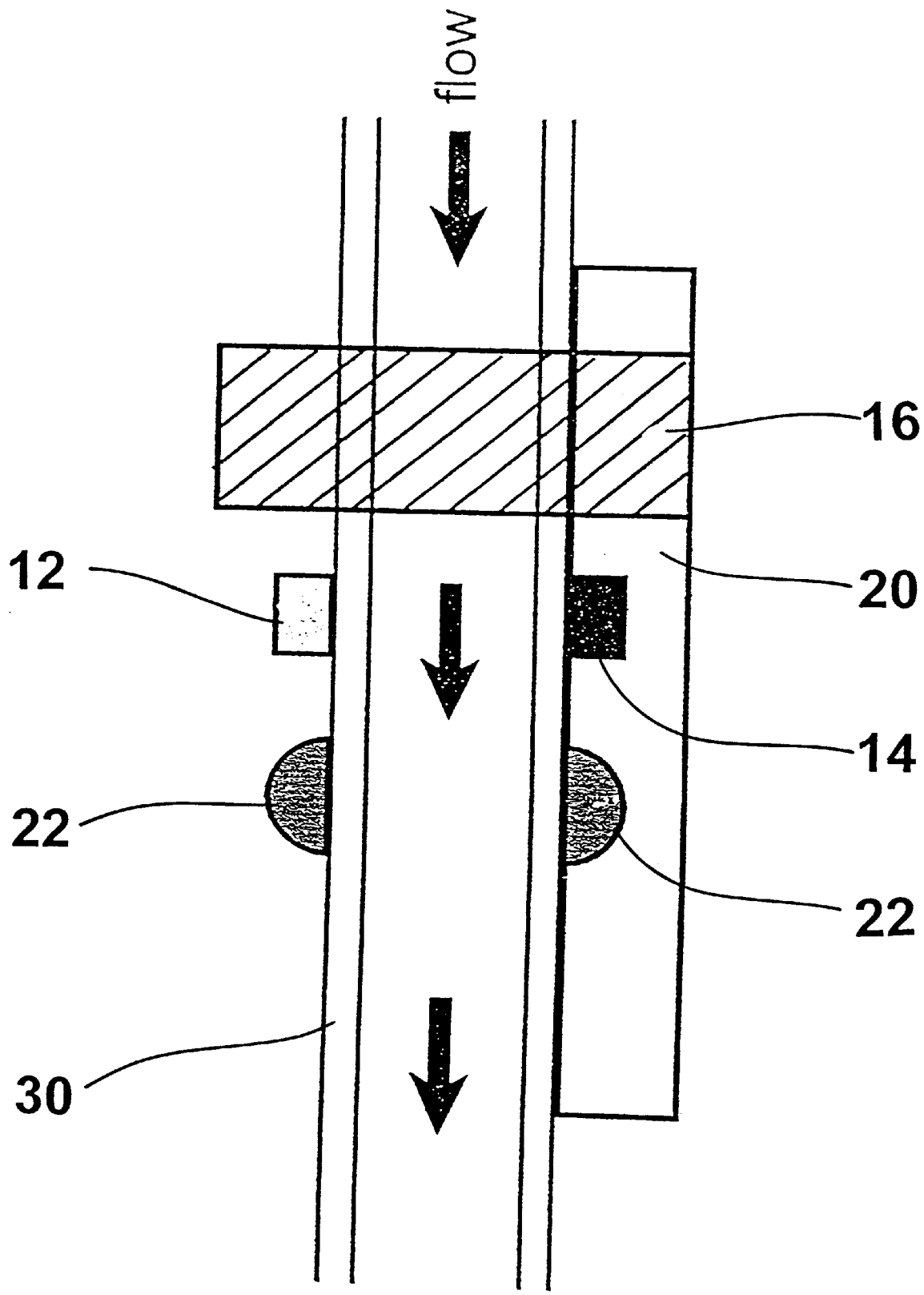
FIG. 9 shows a close-up of an embodiment of the invention for use on tubing.

The description is also intended to include in vitro blood containers such as tubes 30 such as shown in FIG. 9. The reference numerals in FIG. 9 are the same as shown in FIG. 6.

The electromagnetic radiation in this description will refer to light in the visible and infrared range although, as noted in the attached claims, it is conceivable that other forms could be used.

Similarly, while the present invention describes the use of transillumination, it will be appreciated that reflectance spectrophotometry may alternatively be employed.

The absorbance spectra for a great many substances are known, for example, that of glucose. A problem with infrared detection of glucose is that many other substances in blood have similar absorbances in regions of the infrared spectrum. This makes it difficult to differentiate glucose from these other substances. However, all infrared spectra will alter in response to temperature change. By definition, the spectra of different substances will change in different ways, because their molecular configurations are different. Thus, comparison or spectra at varying temperatures will allow separate identification.

OPERATION OF DEVICE

Incident radiation passing through a body part is attenuated (absorbed) in the tissue. The theoretical basis for spectrophotometric techniques is Beer's law (the Beer-Lambert-Bouguer law) which expresses the incident intensity in terms of transmitted intensity and extinction coefficients of the tissue compartments through which the radiation has passed. The equation can be written as:

$$ln(I_o/I)=ECL$$

where $I_o$ is the incident intensity of the source radiation, I is the transmitted intensity of the source through the sample, E is the extinction coefficient of the component of interest, C is the concentration of the component in the tissue itself, and L is the optical path length (distance) through the absorber. Beer's law and the practice of spectrophotometry and oximetry have been exhaustively reviewed in the literature. Pulse oximetry in effect filters out signals other that pulsating (AC). In the body, it can be assumed that the pulsatile component of the signal is arterial blood, while all other tissue absorbers should be non-pulsatile (DC).

A light signal of a known intensity and wavelength is produced by means of light-emitting diodes (LEDs) as in currently used oximeters or, as in the preferred embodiment, a broad-band light source whereby wavelengths are isolated by a rotating filter or diffusion grating. In the latter case, the emitted light is distilled through a filter which allows a known wavelength and intensity of light to penetrate. Use of tunable lasers or other equipment is also possible.

If the light source is proximate to the point of use, no further mode of transmission will be needed. If it is not, the light will be transported to the desired point by means such as a fiber optic cable, preserving the wavelength and intensity.

Several means of temperature induction are possible. Possibilities are convection, conduction from gas or liquid, or radiant energy such as microwaves. As with the light signal, If the heating/cooling source is at or immediately adjacent to the area of need, no further transmission may be needed. If this is not the case, the means will be transported to the desired point by appropriate tubing or cabling.

Various means of temperature measurement are also possible. A large variety of electronic thermistors are commonly available. Other means such as infrared determination may also be used.

A broad-band photo detector (in the case of visible or infrared light) or other means will be utilized to measure the quantity of transmitted light. The wavelength, intensity, and timing of the emitted signal is known, allowing the extinction coefficients for the compartments through which the light passed to be calculated.

To generate a single data point, the temperature induction means is used to bring the finger (or tubing or other space of interest) to a known temperature; a temperature measurement means will be used to confirm the temperature and adjust the temperature induction means if necessary. Light of known wavelength and intensity is emitted (and transmitted if necessary) on the surface of interest. Detection of the light signal at a distinct point (normally opposing surface) is made and the relative absorbance and extinction of the signal is calculated. This measurement may be repeated one or more times to ensure the accuracy of the measurement; this can be done within a very short time frame (less than a millisecond).

Figure 10:
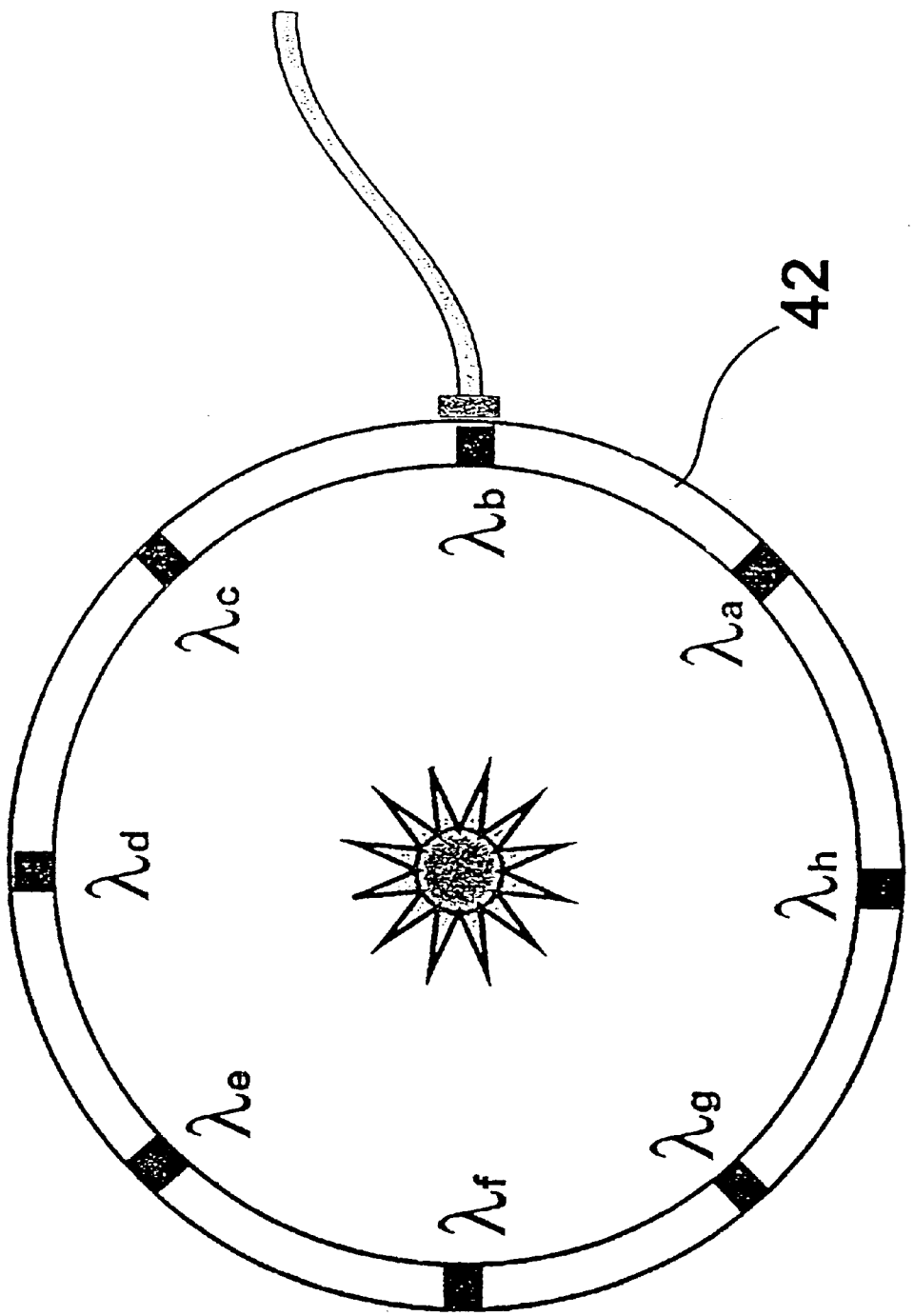
FIG. 10 shows a preferred embodiment for the production and transmission of light radiation. Light of a specific wavelength and intensity is generated and transmitted to the desired site.

To generate multiple data points, the process outlined in the previous step will be repeated at the next chosen wavelength, while still at the same predetermined temperature. In the embodiment described herein, as shown in FIG. 10, the filter 42 would be rotated so that the next wavelength filter would be adjacent to the fiber optic transmission cable. The range and number of wavelengths can be selected, and changed for different applications.

Once the desired number of wavelengths has been examined, the temperature induction means would bring the volume to a predetermined second temperature, and the data collection of steps would be repeated. At the completion of measurements and determinations for this second temperature, the temperature induction means will bring the space to a third predetermined temperature, and the measurements and determinations repeated. This process would be continued until the desired range of temperatures has been scrutinized.

The device can be operated intermittently or continuously. In the intermittent mode, a single set of calculations can be used for analysis to produce the determinations claimed. However, the device can also be easily operated in continuous mode, with the process outlined above repeated as often as wished (constantly if desired). In addition, a rapid ("stat") mode can be offered with the minimum number of measurements made that will provide an accurate estimation of correct values. Such a rapid mode would be useful in emergency situations.

While this methodology should give precise values, further adjustment may be desired to compensate for any discrepancies between theoretical and in vivo measurements. Contemporary oximeters in fact use a calibration curve when determining oxygen saturation, with the curve being generated with data from normal volunteers. A standard calibration curve for a typical oximeter is shown in FIG. 11. If necessary, such a calibration or compensation curve can be created for use with these procedures for performing noninvasive.

CALCULATIONS AND ANALYSIS

The "Henderson-Hasselbach" equation, which is discussed by A. Maas, et. al, "On the reliability of the Henderson-Hasselbalch equation in routine clinical acid-base chemistry", *Annals of Clinical Biochemistry*, Vol. 21, pp 26–39 (1984) is well known in physiologic chemistry, describes the dissolution of an acid in terms of pH, pK (dissolution or dissociation constant), and the concentrations of the acid and its salt or base. The solubility, $\alpha$, of carbon dioxide ($CO_2$) is temperature-dependent, and the pK for $CO_2$ depends on both temperature and pH. For $CO_2$, the Henderson-Hasselbach equation becomes:

$$pH = pK + \log\frac{[HCO_3^-]}{\alpha PCO_2};$$

or an alternate form can be used:

since $[TCO_2]$ is very close to the sum of $[HCO_3^-]$ and $\alpha PCO_2$, $$[TCO_2] = [HCO_3^-] + \alpha PCO_2 \text{ and}$$

$$[HCO_3^-] = [TCO_2] - \alpha PCO_2; \text{ then}$$

$$pH = pK + \log\frac{[TCO_2] - \alpha PCO_2}{\alpha PCO_2}$$

The degree of shift of the HODC is determined using calculations similar to that described below by Nunn (referenced above) and Kelman (G. R. Kelman, "Nomograms for Correction of Blood $PO_2$, $PCO_2$, pH, and Base Excess for Time and Temperature", *Journal of Applied Physiology*, Vol. 21, No. 5. pp 1484–1490, (1966)), and modified by Siggaard-Andersen (referenced above) and others, can be calculated by:

temperature factor=antilog$\{0.024(37\text{-temperature})\}$ pH factor=antilog$\{0.48(pH-7.40)\}$ base excess factor=antilog$\{-0.0013\times\text{base excess}\}$ Calculation of blood oxygen content is made by computations similar to that of Nunn:

content (ml $O_2$/dl)=THb(g/dl)$\times SO_2 \times 1.38$(ml $O_2$/g $HbO_2$)+$0.003 \times PO_2$ Conversion of $PO_2$ to $SO_2$ is done using modifications of Adair's equation or Kelman's computation:

$$SO_2 = (25 \times (0.0257 \times PO_2 + 2 \times 0.00078 \times (PO_2)^2 + 3 \times 0.00000444 \times (PO_2)^3 + 4 \times 0.00000255 \times (PO_2)^4)/$$
$$(1 + 0.0257 \times PO_2 + 0.00078 \times (PO_2)^2 + 0.00000444 \times (PO_2)^3 + 0.00000255 \times (PO_2)^4))$$

calculation of base excess can be done by the following formula or other known means:

base excess=$(1-0.0143\times Hb)\times([HCO_3]-24)$

It should be noted that all stated formulas are subject to change and/or modification, and represent approximate values. Alterations of this algorithm will be suggested to those skilled in the art, and are meant to be included within the scope and spirit of this application.

The following algorithm describes the use of the present invention. Some variables have degrees of co-dependence. In these cases, values are calculated by iterative computational techniques.

Measurement of $SO_2$ is made by a first probe 12 and apparatus 10 comparable to that shown in FIGS. 5 and 6, using methods similar to standard oximetry described in the prior art. The probe is at a set known temperature. Calculation of $PO_2$ is made using computations similar to those described in the references and set forth above. For convenience, this probe may be brought to 37°, in which case the "true $PO_2$" can be calculated without correction for temperature ("normalization" to 37°). If the temperature is in fact a different value, correction may made by methods similar to those described in the references and described above.

Measurement of $SO_2$ is made by a second probe at a different temperature. Alternately, the temperature of the single probe can be changed, and a determination of $SO_2$ made at the new temperature. A higher or lower value of temperature can be used, although for ease of measurement one may be preferable.

Calculation of $PO_2$ is made as above. The difference in $PO_2$ due to the temperature difference (shift in HODC) between the two measurements is factored.

After the temperature change has been factored, any remaining difference is due to a shift in the HODC due to acid-base balance. This is primarily due to pH and only a very small component is due to base excess. The base excess can be computed by other means and then back-factored into the calculated shift in the HODC.

The "pH factor" is calculated from the ratio of the two determinations of $PO_2$.

Correction of the pH factor is made for the known change in pH due to change in temperature. Biochemically, temperature has an effect on the hydrogen ion distinct from the shift in the HODC.

The alteration of pH from normal (7.40) is calculated. If there is no alteration, this implies a pH of 7.40.

Now that the pH is known, computation of the carbon dioxide parameters is done using the Henderson-Hasselbach equation as described above. The effect of temperature on $PCO_2$ is known, as in the consequence of temperature and pH on pK. Thus, $PCO_2$, $[HCO_3^-]$, and $[TCO_2]$ can be computed or calculated by nomograms similar to those elucidated by Siggaard-Andersen (referenced above) and others.

Figure 4:
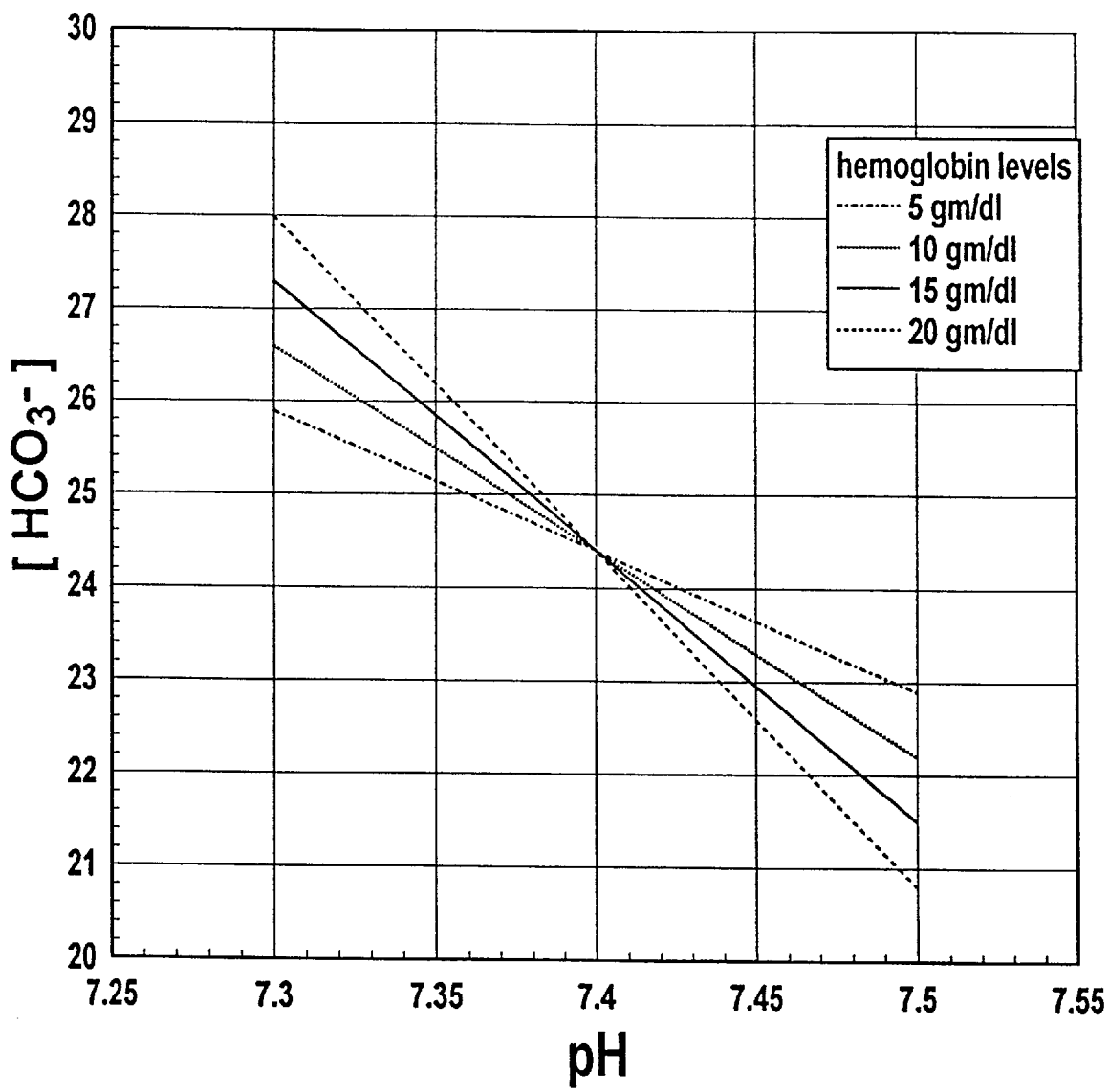
FIG. 4 is a representative graph of the hemoglobin buffering effect in whole blood.

Now that the pH and $[HCO_3^-]$ are known, computation of Hb level can be made by construction of the buffer line of blood as shown in FIG. 4 (see also, Davenport, referenced above). Calculation of base excess is done as in the formula above. As mentioned, base excess can also be computed from a relative shift in the HODC, and this additional computation can serve as a confirmation of Hb level.

Oxygen content is computed as per the calculation above.

As mentioned above, modifications of this algorithm will be suggested to those skilled in the art, and are meant to be included within the scope and spirit of this application. For instance, the case of base excess was cited. Additionally, the effects of 2,3-DPG have been ignored in this description, as they are not normally considered in current clinical practice. Clearly one may wish to take these into account under certain circumstances.

Similarly, the effects oxygen and carbon dioxide have on the transport of each other in blood are described by the Bohr and Haldane effects (together with hemoglobin level). These effects can be used to calibrate and validate results.

Following are examples which illustrate procedures for practicing the invention. These should not be construed as limiting, and that various modifications will be suggested to persons skilled in the art and are to be included within the spirit and purview of this application and the scope of the appended claims.

EXAMPLE 1

Figure 5A:
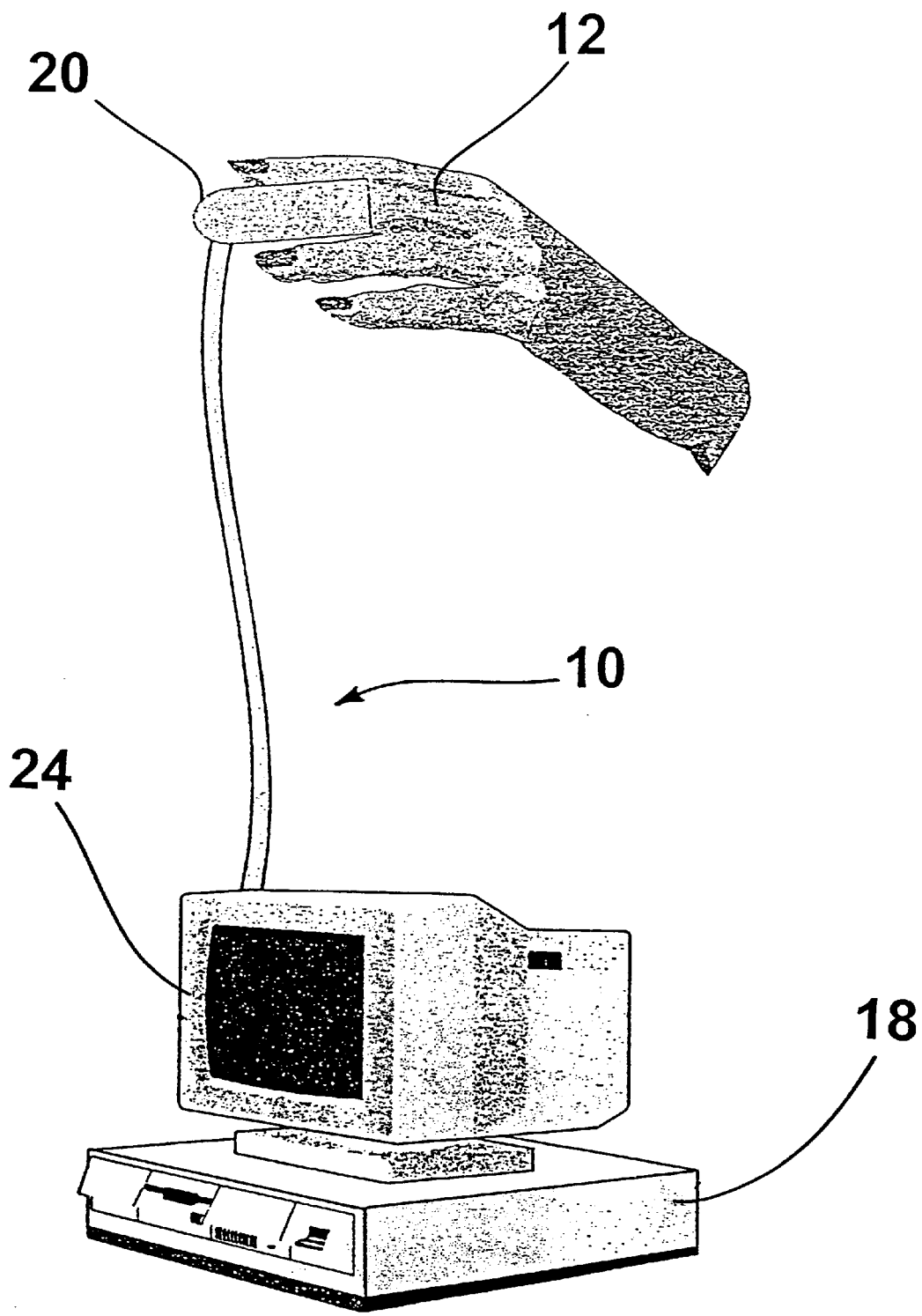
FIG. 5a shows an embodiment of the invention for use on a finger. As mentioned in the text, any part of the body that can be successfully transilluminated with the radiant energy used can be utilized. Thus, toes, lips, etc. could also be used.

A single probe 20 similar to that illustrated in FIGS. 5a and 6 is used. Measurement of $SO_2$ is made by use of a light signal 12 and photo detector 14. The heating/cooling element 16 in the probe 20 is then used to raise the temperature of the finger (F) to approximately 40° C. A second measurement of $SO_2$ then is made. The algorithm outlined above is used by a computing device 18 to calculate all relevant variables which can be displayed on a monitor 24 for evaluation by a user.

A device 10 such as this might be used in place of laboratory analysis for stable patients or part of routine physical diagnosis, where the parameters are expected to change very little over the course of several minutes.

EXAMPLE 2

Figure 5B:
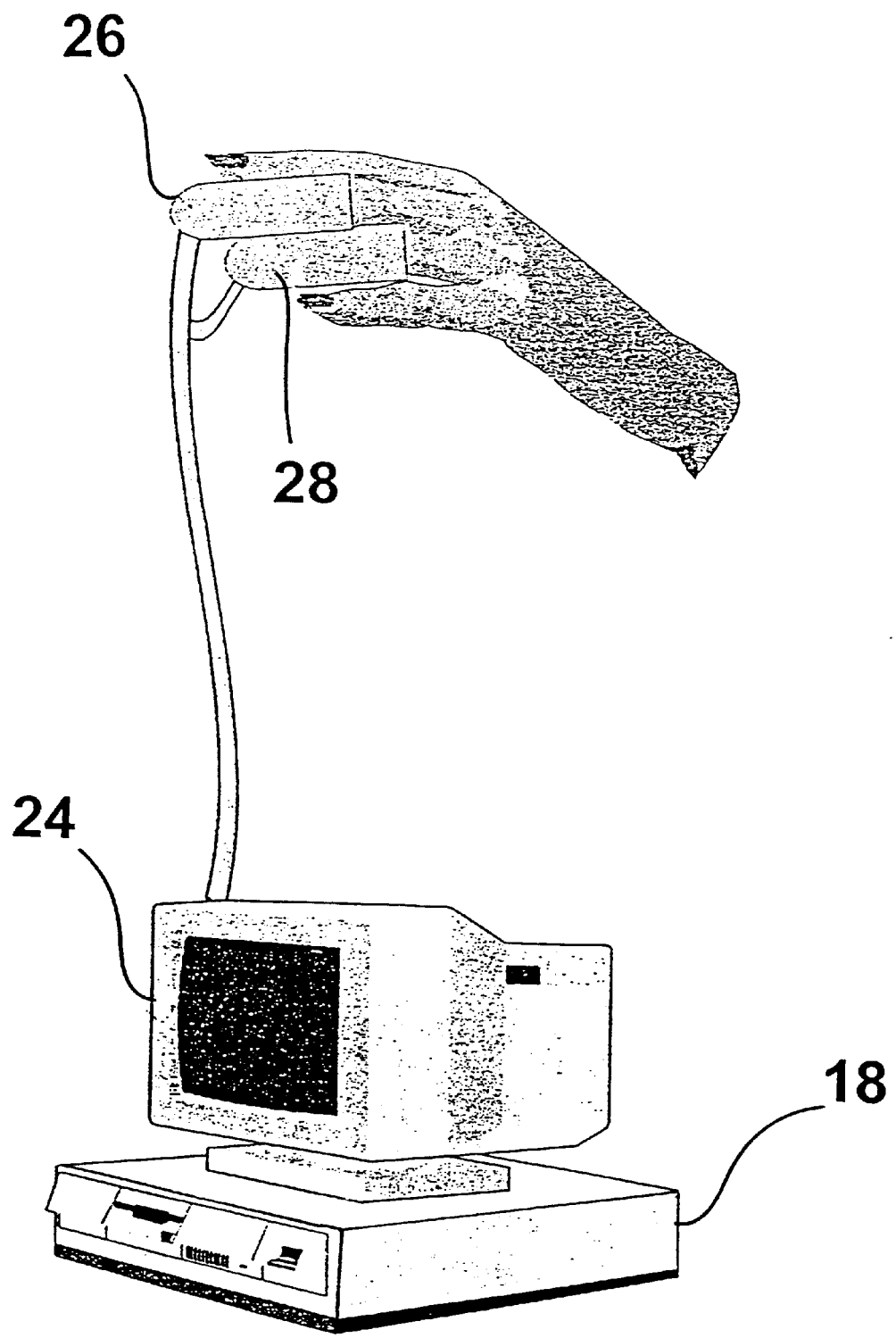
FIG. 5b shows an embodiment of the invention using two fingers.

Two probes 26 and 28 similar to that illustrated in FIG. 5b are used. The heating/cooling element 16 in one of the probes is used to raise the temperature of its finger to approximately 40° C. Simultaneous measurements of $SO_2$ are made by the two probes, one probe at body temperature and the other probe at the raised temperature. The algorithm outlined above is used to calculate all relevant variables.

Figure 7:
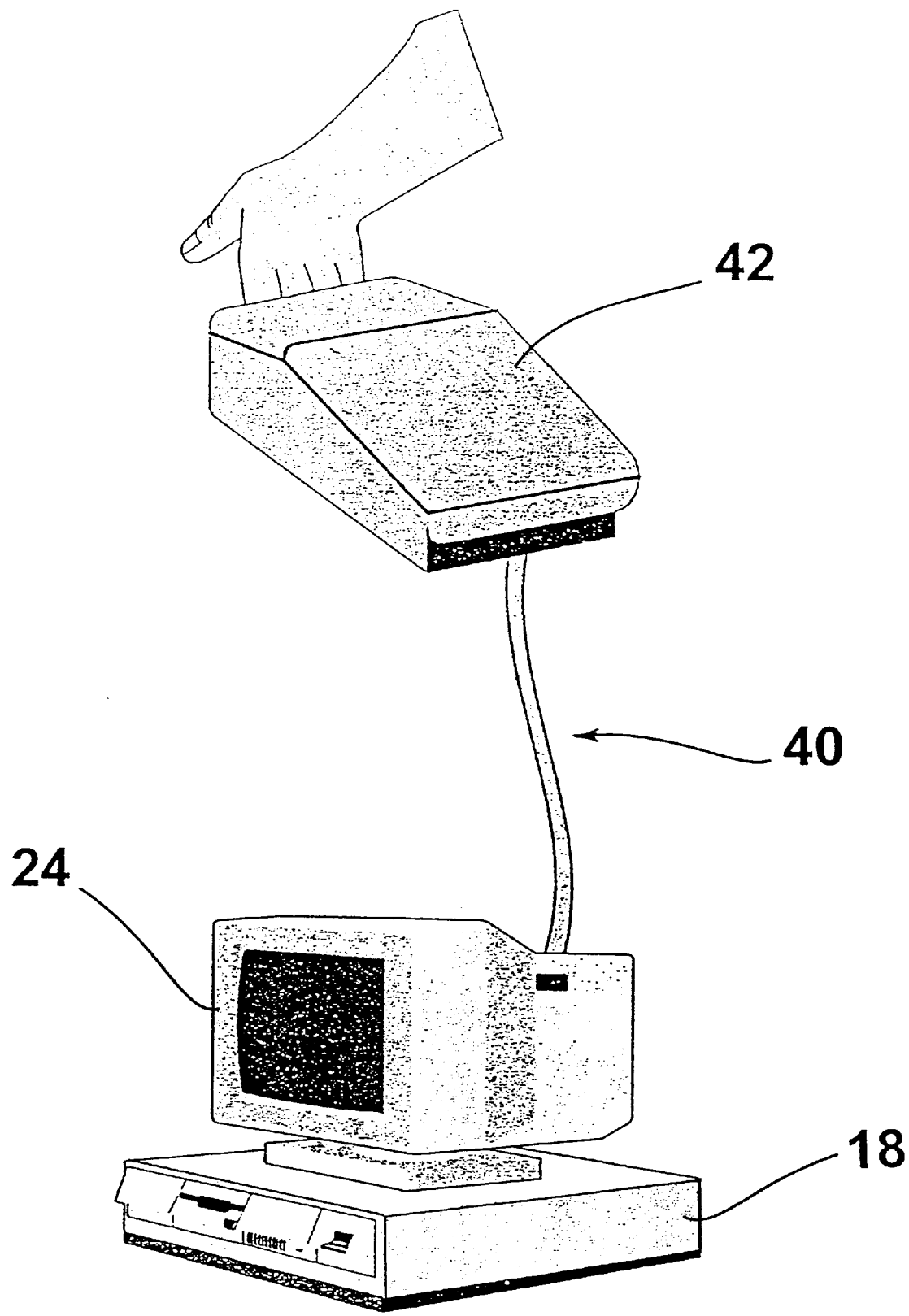
FIG. 7 shows an embodiment of the invention whereby fingers are placed inside a housing. This embodiment allows multiple simultaneous measurements to be made. The radiation source, emitters and detectors, and heating/cooling means would all be contained within the casing. The processing, entry, and display units could also be housed within the casing for a single self-contained assemblage.
Figure 8:
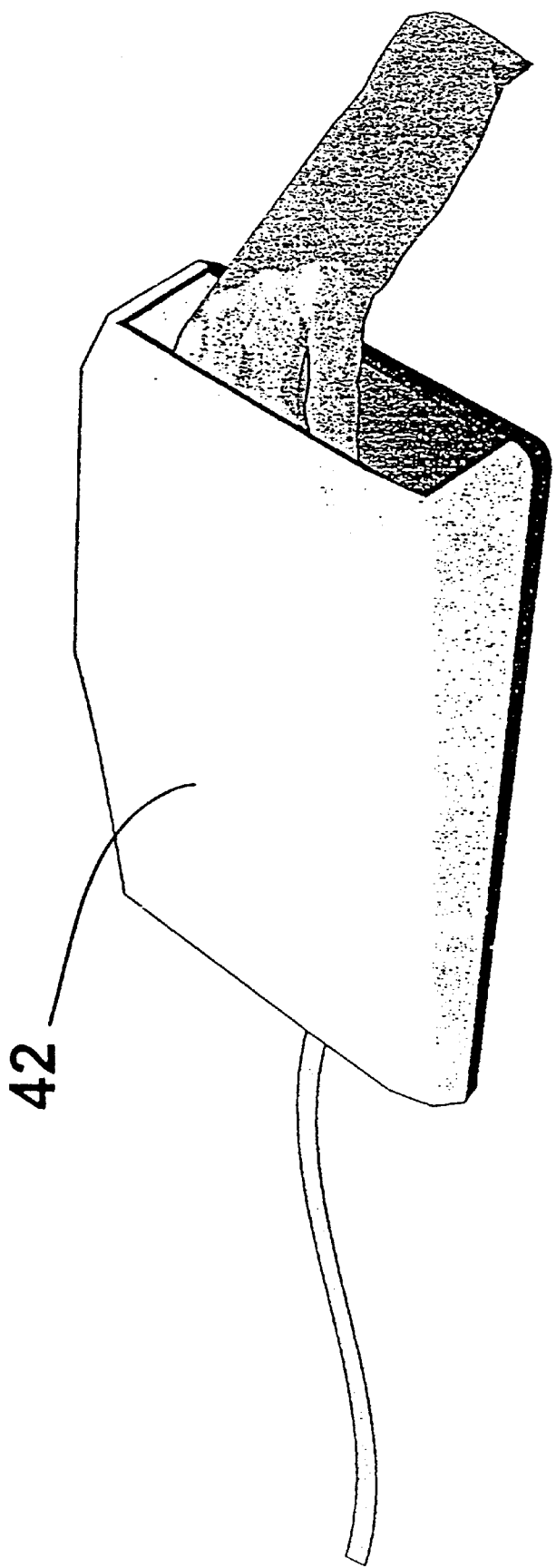
FIG. 8 shows a close-up of an embodiment of a casing containing elements of the invention.

Alternatively, the embodiment shown in FIGS. 7 and 8 is used. A device 40 such as this might be used during anesthesia for brief or low-risk surgery, where the parameters might be expected to change somewhat over the course of several minutes. The device 40 is provided with a hand and finger housing 42 which receives several fingers of a human patient within the housing. A single or multiple probes similar to that shown in FIG. 6 can be provided in the housing with respective heating/cooling elements.

EXAMPLE 3

Figure 5C:
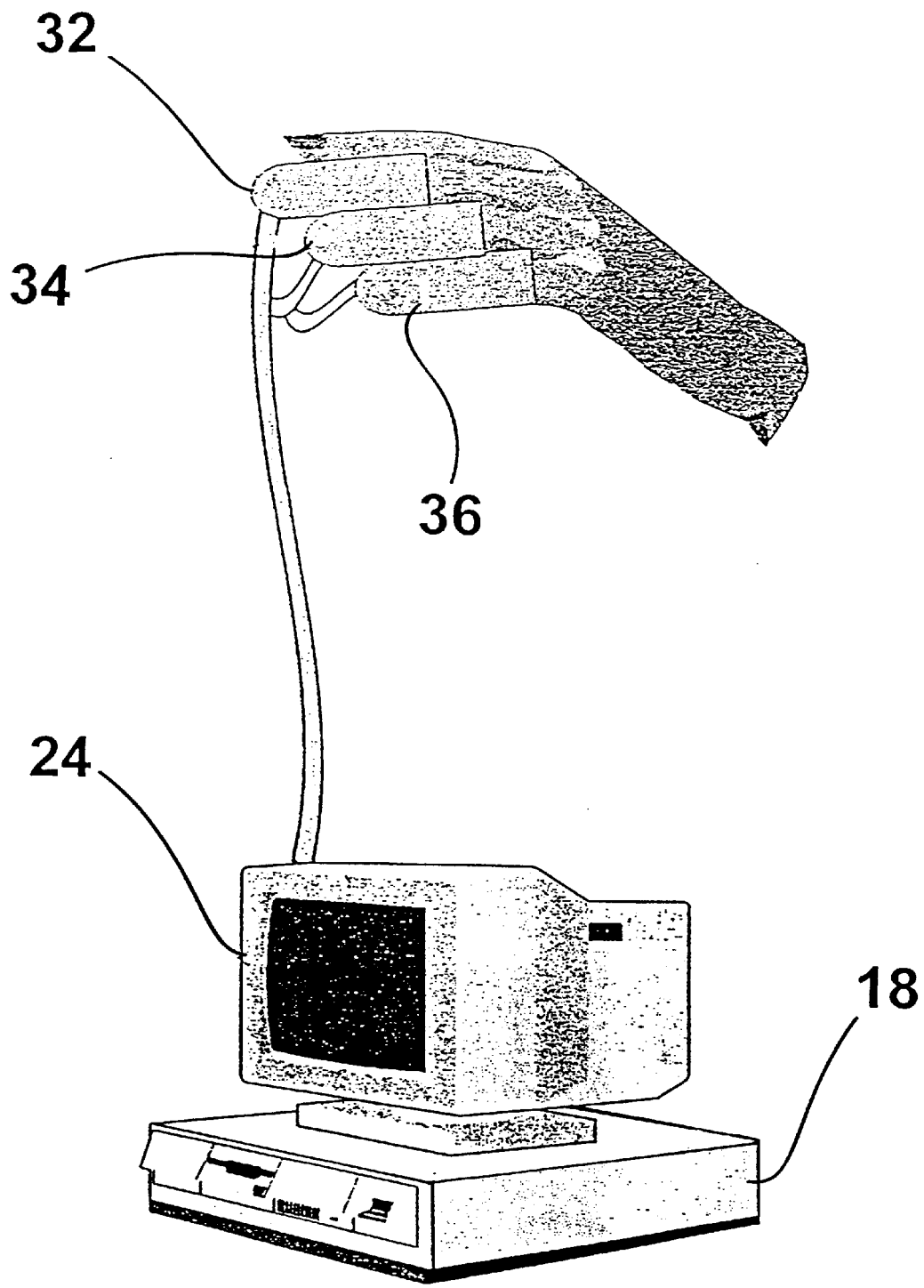
FIG. 5c shows an embodiment of the invention using three fingers.

Three probes 32, 34, and 36 similar to that illustrated in FIG. 5c are used. A first probe 32 is used without heating or cooling the respective finger. The heating/cooling device 16 in a second probe 34 is used to raise the temperature of one finger to approximately 40° C. The heating/cooling device 16 in a third probe 36 is used to lower the temperature of a respective third finger to approximately 33° C. Simultaneous measurements of $SO_2$ are made by the three probes 32, 34, and 36. The algorithm outlined above is used by a computing device to calculate all relevant variables.

Alternatively, the embodiment shown in FIGS. 7 and 8 having multiple finger probes could be used.

A device such as this might be used in emergency rooms, critical care units, or during anesthesia for high-risk patients, where there is concern that the determined parameters might change very rapidly, and also where significantly lower values of $SO_2$ and $PO_2$ may occur.

EXAMPLE 4

Two probes 20 similar to that illustrated in FIG. 9 are used. The heating/cooling device 16 in one of the probes is used to raise the temperature of its tubing 30 and contents to approximately 40° C. Simultaneous measurements of $SO_2$ are made by the two probes. The algorithm outlined above is used to calculate all relevant variables.

A device such as this might be used during hemodialysis, where the blood is circulated in tubing outside the body, and parameters might expected to change over the course of several minutes.

EXAMPLE 5

Three probes 20 similar to that illustrated in FIG. 9 are used. The heating/cooling devices 16 in the probes are used to bring the temperatures of three separated pieces of tubing 30 and their contents to 33°, 37°, and 40°, respectively. Simultaneous measurements of $SO_2$ are made by the three probes. The algorithm outlined above is used to calculate all relevant variables.

A device such as this might be used during cardiopulmonary bypass, where the blood is circulated in tubing outside the body, and parameters might be expected to change rapidly.

EXAMPLE 6

A single probe 20 similar to that illustrated in FIGS. 5a and 6 is used. The heating/cooling device 16 in the probe is used to vary the temperature of the finger from 33° C. to 40° C. in increments of 1° C. Measurements of $SO_2$ are made at the differing temperatures. The algorithm outlined above is used to calculate all relevant variables.

In this manner, a series of data is collected for improved accuracy in performing calculations.

Comparably, an example with a single probe 20 for tubing 30 similar to that in FIG. 9 is envisioned.

EXAMPLE 7

Two or more probes 20 similar to that illustrated in FIGS. 5a and 6 is used. The heating/cooling device 16 in the probes are used to vary the temperatures of the fingers from 33° C. to 40° C. in increments of 1° C. Measurements of $SO_2$ are made at the differing temperatures. The algorithm outlined above is used to calculate all relevant variables.

In this manner, a series of data is collected for improved accuracy in performing the calculations.

Comparably, an example with two or more probes 20 for tubing 30 similar to that in FIG. 9 is envisioned.

EXAMPLE 8

A single probe similar to that illustrated in FIGS. 5a, 5b, 5c, and 6 are used. Absorbance of emitted radiation over several wavelengths is measured.

A device such as this might be used to measure glucose, potassium, urea, creatinine, or other blood constituents. It could also detect substances not normally present in blood (or present in very small quantities) such as fetal hemoglobin, myoglobin, etc.

Comparably, examples with two or more probes for tissue or tubing are envisioned.

It is clear from the prior art cited that the invention described herein will measure the presence of other substances in blood in a manner equal, and in many cases superior, to current techniques.

EXAMPLE 9

A single probe 20 similar to that illustrated in FIG. 9 is used. Instead of blood, measurements are made from a different body fluid such as urine, using the tubing from a bladder catheter.

A device such as this might be used to measure glucose, urea, creatinine, or the excretion of some substance in the urine.

Comparably, examples with two or more probes 20 for tissue (T) or tubing 30 can be utilized as discussed above.

EXAMPLE 10

A single probe 20 similar to that illustrated in FIGS. 5a and 6 is used. A multitude of wavelengths is scanned. Detection of ingested drugs, medications, or other substances, or their metabolites, is made. Similarly, substances which appear within the body after other types of exposure, such as inhalation, can be measured.

Comparably, examples with two or more probes 20 for tissue (T) or tubing 30 can be utilized.

A device of this nature may be used in the workplace, hospital emergency rooms, or laboratories. Diagnosis of carbon monoxide poisoning (carboxyhemoglobin level) will be made rapidly and noninvasively. Even more importantly, the consequences of this poisoning, in the form of reduction in oxygen carrying capacity and metabolic acidosis, will be quickly known, allowing appropriate therapy to be chosen (oxyhemoglobin, carboxyhemoglobin, oxygen content, and pH can all be measured with the present invention). The results of therapy can be monitored continuously, and as long as necessary.

EXAMPLE 11

A single probe 20 similar to that illustrated in FIGS. 5a and 6 is used. A multitude of wavelengths is scanned. Screening of sickle cell disease or trait or other hemoglobinopathies can be done quickly and noninvasively for large populations. Results can be confirmed by traditional laboratory analysis.

Comparably, examples with two or more probes 20 for tissue (T) or tubing 30 can also be utilized.

It is within the scope of this invention for diagnosis of other diseases or conditions which can be distinguished by markers in blood or other substances carried in blood or other body fluids. Examples include blood typing, screening of potential donors for bone marrow transplantation, certain cancers, etc.

EXAMPLE 12

Emitters and detectors can be arranged in serial pairs or a like configuration in probes similar to those in FIGS. 5 and 6. This would enable calculations made in the time or frequency domain, such a wave or pulse velocity. Emitters and detectors can be also grouped in parallel or concentric arrangement in probes similar to those in FIGS. 5 and 6. This would enable multidimensional analysis, c omparable to computerized tomography.

EXAMPLE 13

The use of the present invention in monitoring of water or other liquids is also envisioned. A mechanism could be easily constructed whereby a modification of the invention could be placed "in-line" for the water system of a building or city. In this manner the quality and purity of the water are constantly monitored and protected. The light absorption characterist ics of an enormous number of substances are known, and can thus be screened for by the method of the present invention. Toxins, contaminants, or undesired substances can be detected and recognized quickly and easily, and appropriate measures instituted.

The sampling would not in any way affect the water or liquid, and the fluid would never leave its existing containers, such that samples would not have to be collected or disposed of in environmentally safe methods.

EXAMPLE 14

The use in monitoring of air or other gases is also envisioned. A mechanism in which samples of air from a building or industrial plant are continually monitored. As mentioned in the previous example, the light absorption characteristics of a large number of substances are well documented, and these elements can be detected using this technique. Air quality can be monitored on a constant basis. Atmospheric sampling can be performed.

EXAMPLE 15

The in vitro utilization of this invention is further envisioned. Samples of blood or other body fluids can be taken, stored, and analyzed using the device at a later point. While some characteristics of blood or biologic fluids change over time, these changes are also well known, and the original characteristics can often be inferred.

In the same line of reasoning, the invention may be used to investigate changes and alterations in blood or other substances over time or after subjecting the blood or other substance to some intervention. This is because the invention is noninvasive and nondestructive.

EXAMPLE 16

The use in remote sensing applications is possible. Infrared techniques for distant temperature sensing are in use. When combined with the present invention, one may be able to measure many biochemical processes remotely as well. This will assist in the study of atmospheric and other pollution, and a myriad of additional processes.

EXAMPLE 17

The use in environmental studies, such as the investigation of global warming, is foreseen. Substances are sought as markers which indicate temperature changes over a period of time. This invention will aid in this by identifying changes due to temperature.

EXAMPLE 18

A broad range of additional applications is envisioned. Ultraviolet and Xay radiation are used in the technical analysis of artwork to assist in the stablishment authenticity and age. Modifications of this invention will help in ondestructive testing by detection of substances within such works.

EXAMPLE 19

It is known that the infrared absorbance spectrum of water changes with temperature. The absorbance spectra of elements contained within water (contaminants, pollutants, or other substances) will also change with temperature. The spectra of these substances will change in a different manner than the spectrum of water. Thus, use of temperature pertubation or other agitation may greatly aid in analysis of such substances, without having to change the primary detection means. Many types of analysis tools and techniques currently in use could be greatly improved without large investment or retooling. Future analysis techniques could be developed utilizing this methodology to assist in measurements.

Other variables or parameters not mentioned above an also be measured or estimated. For example, the hematocrit is commonly estimated as three times the hemoglobin level. As the primary determinants of blood viscosity are temperature and hematocrit, this can be estimated, which allows additional calculations of pressure, vessel elasticity, etc.

The use of multiple or broad spectrum wavelength emission and detection (possibly combined with appropriate filters) enables the identification of a multitude of blood constituents, either naturally occurring or as the product of metabolism or pharmacokinetics. The identification of certain substances and their concentrations allows their use as references for determination of others.

Hemoglobins are found in all classes of vertebrates, in most invertebrate phyla, and even in some plants. Other respiratory pigments such as chlorocruorins, hemerythrins, and hemocyanins are found in other organisms. The function of all is dependent upon temperature and pH. Similarly, plants contain the molecule chorophyll in several forms. This substance is closely related to the hemoglobins of animal systems, and is also extremely sensitive to temperature changes. A multitude of other molecules, such as phosphorus compounds like the adenosine phosphates (ATP and others), found in both plants and animals, are reactive to temperature variation. The technology outlined in this patent application is relevant to measurements and determinations for all these substances and, in many cases, the environments or milieu in which they exist.

The technique may be utilized on homogeneous elements or matter which is a combination of substances.

It should be understood that the examples and embodiments described herein are for illustrative purposes only, and that various modifications and embodiments will be suggested to persons skilled in the art. The claims are meant to include all such modifications and embodiments.

I claim:

1. A radiation delivery device for facilitating the noninvasive monitoring of a characteristic of a patient's blood parameters, the device comprising:

a radiation emitter having at least one wavelength and adapted to be directed at the patient's blood;

a radiation detector which detects said at least one wavelength after absorbance through said blood;

a temperature induction generator for inducing at least two different temperature levels in said blood; and a controller for computing the various characteristics of the patient's blood parameters based on the absorbance of said at least one wavelength of radiation at various temperature levels of said blood.

2. The radiation delivery device of claim 1 wherein the radiation is selected from the group of visible light, infrared light, and ultraviolet light.

3. The radiation delivery device of claim 1 wherein the radiation emitter has at least one wavelength adapted to be directed at a patient's tissue including blood, and said radiation detector detects said at least one wavelength after absorbance through said tissue.

4. The radiation delivery device of claim 3, wherein said tissue is selected from the group consisting of hands, fingers, feet, toes, ears, earlobes, nares, lips, and tongue.

5. The radiation delivery device of claim 3, wherein the temperature induction generator raises the temperature of the patient's tissue including blood.

6. The radiation delivery device of claim 5, wherein the temperature induction generator raises the temperature of the patient's tissue including blood to about 40° C.

7. The radiation delivery device of claim 3, wherein the temperature induction generator lowers the temperature of the patient's tissue including blood.

8. The radiation delivery device of claim 7, wherein the temperature induction generator lowers the temperature of the patient's tissue including blood to about 33° C.

9. The radiation delivery device of claim 3, wherein the temperature induction generator raises and lowers the temperature level of the patient's tissue including blood; and said controller for computing the various characteristics of the patient's blood parameters computes the various characteristics based on the absorbance of said at least one wavelength of radiation at each of three temperature levels of said tissue including blood.

10. The radiation delivery device of claim 9, wherein the temperature levels are about 33°, 37°, and 40°, respectively.

11. The radiation delivery device of claim 1, wherein the patient's blood is carried in tubing, and the radiation emitter is applied to said tubing and contents, the radiation detector detects through said tubing and contents, said temperature induction generator induces temperature changes in said tubing and contents, and said controller computes the various characteristics of the patient's blood parameters based on absorbance of said at least one wavelength of radiation at various temperature levels of said tubing and contents.

12. A radiation delivery device of claim 11, where the temperature induction generator raises and lowers the temperature level of the tubing and blood contents; and the controller for computing the various blood parameters measures the absorbance of said radiation at three temperature levels of said tubing and blood contents.

13. A radiation delivery device of claim 1, further comprising a plurality of radiation emitters, and respective radiation detectors and temperature induction generators, each respective emitter, detector and temperature induction generator being set at a different temperature level so that said controller can simultaneously measure the absorbance of said radiation at said various temperature levels of said blood.

14. A device to detect and measure elements of blood, including, but not limited to, hemoglobin in any of its forms, comprising:

radiation emission means;

detecting means for receiving said radiation after contact with the blood;

means for inducing a temperature change in the blood;

means for measuring the temperature of the blood;

controller means for computing the various elements of the blood based on contact of said radiation from said radiation emissions means at various temperature levels of the blood, the controller means having input means to allow various changes in the radiation emission means, detecting means, and temperature inducing means;

and a display means to indicate the various elements of the blood to an end user of the device.

15. A device of claim 14, wherein the radiation emitted by said radiation emission means is selected from the group consisting of visible light, infrared light, and ultraviolet light.

16. A device of claim 14, wherein the means for inducing temperature changes in said blood is selected from the group consisting of conduction, convection and radiation.

17. A device of claim 14, wherein the means to measure temperature of said blood is selected from the group consisting of electronic, and infrared.

18. A device of claim 14, further comprising of plurality of respective radiation emission means, detection means, means for induction of temperature change, and means for measuring temperature.

19. A method for noninvasively determining one or more of the following blood parameters; total hemoglobin, oxygen saturation, partial pressure of oxygen, partial pressure of carbon dioxide, bicarbonate ion, total carbon dioxide, acid-base balance, base excess, oxyhemoglobin, and oxygen content, in an animal or human, said method comprising of steps of:

emitting radiation having at least one wavelength to the blood:

detecting said radiation having at least one wavelength after said radiation contacts the blood;

inducing a temperature change in said blood while emitting and detecting said radiation through the blood; and computing the blood parameters based on the contact of said at least one wavelength of radiation at various temperature levels of the blood.

20. The method of claim 19, wherein said detecting step is selected from the group consisting of detecting said radiation after absorbance, reflection, and any combination thereof with the blood.

21. The method of claim 19, wherein said radiation is selected from the group consisting of visible light, and ultraviolet light, or any combination thereof.

22. The method of claim 19, wherein the inducing a temperature change step includes conduction, convection, and radiation or any combination thereof.

23. The method of claim 19, further including a step of measuring the temperature of the blood.

24. The method of claim 19, wherein said emitting step includes the emission of a plurality of wavelengths to the blood.

25. The method of claim 19, wherein said blood is contained in animal or human tissue and the radiation contacts said tissue.

26. The method of claim 25, wherein said tissue is selected from the group consisting of hands, feet, toes, ears, earlobes, nares, lips, and tongue.

27. The method of claim 20, wherein said blood is contained in a tube outside of the animal or human tissue and the radiation is emitted through said tube.

28. A device for noninvasively determining characteristics of subject matter and the e nvironment in which the subject matter exists, the device comprising:

emitter means having at least one wavelength of electromagnetic radiation applied to the subject matter;

detector means for sensing and measuring reception of said wavelength after contact with the subject matter;

temperature induction means for generating temperature changes in the subject matter; and a controller for manipulating said emitt er means, detector means, and temperature induction means and for computing parameters based on information processed from the contact of said radiation at various temperature levels on the subject matter.

29. A devic e of claim 28, wherein the subject matter is a living organism and the characteristics determined are temperature induced changes in biologic molecules.

30. A device of claim 28, wherein the detector means senses and measures reception of s aid wavelength after absorbance by said subject matter.

31. A device of claim 28, wherein the detector means senses and measures reception of said wavelength after reflection from the subject matter.

32. A device of claim 28, wherein the detector means senses and measures reception of said wavelength after refractance from the subject matter.

33. A device according to claim 28, wherein the controller utilizes induced changes in temperature levels to effect alterations in the hemoglobin-oxygen dissociation curve, for noninvasively determining one or more of the following blood parameters;

oxygen saturation, partial pressure of oxygen, partial pressure of carbon dioxide, concentration of bicarbonate ion and total carbon dioxide, acid-base balance, base excess, hemoglobin level, oxyhemoglobin le vel, deoxyhemoglobin level, and oxygen content.

34. A method for facilitating the noninvasive determination of characteristics of subject matter and the environment in which said subject matter exists, the method comprising the steps of:

emitting at least one wavelength of electromag netic radiation applied to said sub ect matter detecting said wavelength after contact with said subject matter;

inducing a temperature change in said subject matter while emitting and detecting said radiation applied to said subject matter; and computing parameters based on information processed from the contact of said radiation at various temperature levels on said subject matter.

35. The method of claim 34, wherein said detection step is selected from the group consisting of detecting said radiation after absorbance, reflection, and any combination thereof with the subject matter.

36. The method of claim 34, wherein the inducing a temperature change step includes conduction, convection, and radiation or any combination thereof.

37. The method of claim 34, further including the step of measuring the temperature of the subject matter.

38. The method of claim 34, wherein said emitting step includes the emission of a plurality of wavelengths to the subject matter.

39. A method for determination of hemoglobin level by means of measuring hemoglobin buffering effect in blood, the method comprising the steps of:

determining the pH of the blood, calculating the bicarbonate ion, and estimating the hemoglobin buffering effect by comparing the pH and bicarbonate ion levels together, then computing the total hemoglobin level therefrom.

40. A radiation delivery device for facilitating the noninvasive monitoring of a characteristic of a substance, the device comprising:

a radiation emitter having at least one wavelength of radiation directed on the substance;

a radiation detector which detects reception of said at least one wavelength of radiation after contact said substance;

a temperature induction generator for inducing temperature changes in the substance; and a controller for computing the various substance parameters based on the absorbance of said at least one wavelength of radiation at said various temperature levels of the substance.

41. The radiation delivery device of claim 40 wherein the radiation is selected from the group consisting of visible light, infrared light, and ultraviolet light.

42. The radiation delivery device of claim 40 wherein the radiation emitter has at least one wavelength being applied to the substance, and said radiation detector detects reception of said at least one wavelength after absorbance through said substance.

43. The radiation delvery device of claim 42, further including at least two radiation emitters wherein the radiation emitters are positioned a first predetermined distance apart, and respective radiation detectors positioned a second predetermined distance apart.

44. The radiation delivery device of claim 40, wherein the temperature induction generator raises the temperature of the substance.

45. The radiation delivery device of claim 40, wherein the temperature induction generator lowers the temperature of the substance.

46. The radiation delivery device of claim 40, wherein the temperature induction generator raises and lowers the temperature of the substance; and said controller for computing the characteristics of the substance based on the absorbance of said at least onw wavelength of radiation at each of three temperature levels of said substance.

47. The radiation delivery device of claim 40, wherein the substance carried in tubing, and the radiation emitter is applied to said tubing and contents, the radiation detector detects through said tubing and contents, said temperature induction generator induces temperature changes in said tubing and contents, and said controller is computing the characteristics of the substance based on the absorbasnce of said at least one wavelength of radiation at various temperature levels of said tubing and contents.

48. A radiation delivery device of claim 33, where the temperature induction generator raises and lowers the temperature level of the tubing and substance; and the controller for computing the various substance parameters measures the absorbance of said radiation at three temperature levels of said tubing and substance.

\* \* \* \* \*

UNITED STATES PATENT AND TRADEMARK OFFICE
CERTIFICATE OF CORRECTION

PATENT NO. : 5,978,691
DATED : November 2, 1999
INVENTOR(S) : Alexander K. Mills It is certified that error appears in the above-identified patent and that said Letters Patent is hereby corrected as shown below:

A. TYPOGRAPHICAL ERRORS
In the Specification

Column 4,
Line 15, change "used In the" to read --used in the --.

Column 5,
Line 50, correct the spelling of "Appied" to read --Applied--.
Line 52, change the spelling of "Bufterworth" to read --Butterworth--.

Column 8,
Line 54, change "signal, If the" to read --signal, i.e., if the--.

Column 14,
Line 34, delete the extra space in "c omparable" to read --comparable--.
Line 44, delete the extra space in "characterist ics" to read --characteristics--.

Column 15,
Line 29, change the spelling of "Xay" to read --X-ray--.
Line 30, correct the spelling of "stablishment authenticity" to read --establishment of authenticity--.
Lines 31-32, correct the spelling of "ondestructive" to read --nondestructive--.

UNITED STATES PATENT AND TRADEMARK OFFICE
CERTIFICATE OF CORRECTION

PATENT NO. : 5,978,691                    Page 2 of 3
DATED      : November 2, 1999
INVENTOR(S) : Alexander K. Mills It is certified that error appears in the above-identified patent and that said Letters Patent is hereby corrected as shown below:

A. TYPOGRAPHICAL ERRORS (continued)
In the claims

Column 18,
Line 26, (claim 28, line 2), change "e nvironment" to read --environment--.
Line 34, (claim 28, line 10), change "emitt er" to read --emitter--.
Line 39, (claim 29, line 1), change "devic e" to read --device--.
Line 43, (claim 30, line 2), change "s aid" to read --said--.
Line 59, (claim 33, line 9), change "le vel" to read --level--.
Line 65, (claim 34, line 5), change "electromag netic" to read --eletromagnetic--.
Line 66, (claim 34, line 6), change "sub ect" to read --subject--.

Column 20,
Line 24, (claim 46, line 5), change "onw" to read --one--.
Line 33, (claim 47, line 7), change "absorbasnce" to read --absorbance--.

B. MATERIAL ERRORS
In the claims

Column 16,
Line 31, (claim 1, line 12), change "various" to read --the at least two different--.

Column 17,
Line 36, (claim 14, line 16), delete "a" before "display".
Line 56, (claim 19, line 5), after "oxyhemoglobin," insert --deoxyhemoglobin,--.

Column 18,
Line 6, (claim 21, line 2), after "visible light," insert --infrared light,--.
Line 22, (claim 27, line 1), change "20" to read --19--.

UNITED STATES PATENT AND TRADEMARK OFFICE
CERTIFICATE OF CORRECTION

PATENT NO. : 5,978,691
DATED : November 2, 1999
INVENTOR(S) : Alexander K. Mills It is certified that error appears in the above-identified patent and that said Letters Patent is hereby corrected as shown below:

Column 19,
Line 24, (claim 39, line 4), start the portion of the line beginning with "calculating" on a new line, indent to be below and aligned with "determining".
Line 36, (claim40, line 7), after "contact" insert --with--.

Column 20,
Line 28, (claim 47, line 2), after "substance" insert --is--.
Line 36, (claim 48, line ), change "33" to read --47--.

Signed and Sealed this

Nineteenth Day of June, 2001

*Attest:*

*Attesting Officer*

NICHOLAS P. GODICI
*Acting Director of the United States Patent and Trademark Office*